(12) United States Patent
Zhang

(10) Patent No.: US 10,878,061 B2
(45) Date of Patent: Dec. 29, 2020

(54) DATA ANALYSIS SYSTEM AND ANALYSIS METHOD THEREFOR

(71) Applicant: Han-Wei Zhang, New Taipei (TW)

(72) Inventor: Han-Wei Zhang, New Taipei (TW)

(*) Notice: Subject to any disclaimer, the term of this patent is extended or adjusted under 35 U.S.C. 154(b) by 303 days.

(21) Appl. No.: 15/966,249

(22) Filed: Apr. 30, 2018

(65) Prior Publication Data

US 2018/0322096 A1 Nov. 8, 2018

(30) Foreign Application Priority Data

May 5, 2017 (CN) .......................... 2017 1 0312459

(51) Int. Cl.
*G06F 17/18* (2006.01)
*G06N 7/00* (2006.01)
*G16H 50/70* (2018.01)
*G06F 16/903* (2019.01)
*G06F 16/904* (2019.01)
*G06F 16/26* (2019.01)
*G06F 16/2458* (2019.01)
*G16H 50/30* (2018.01)

(52) U.S. Cl.
CPC .......... *G06F 17/18* (2013.01); *G06F 16/2465* (2019.01); *G06F 16/26* (2019.01); *G06F 16/903* (2019.01); *G06F 16/904* (2019.01); *G06N 7/00* (2013.01); *G16H 50/30* (2018.01); *G16H 50/70* (2018.01); *G06F 2216/03* (2013.01)

(58) Field of Classification Search
None
See application file for complete search history.

(56) References Cited

U.S. PATENT DOCUMENTS

| | | | | |
|---|---|---|---|---|
| 8,055,603 B2* | 11/2011 | Angell | ................... | G06N 5/025 706/47 |
| 9,213,702 B2* | 12/2015 | Chen | ................... | G06F 16/3325 |
| 9,857,297 B2* | 1/2018 | Hilscher | ............ | G01N 21/3586 |
| 2012/0171650 A1* | 7/2012 | Warner | .............. | A61B 5/04021 434/262 |
| 2016/0378634 A1* | 12/2016 | Jovanovic | ........... | G06F 11/3034 707/688 |

* cited by examiner

Primary Examiner — Kim T Nguyen
(74) Attorney, Agent, or Firm — Birch, Stewart, Kolasch & Birch, LLP

(57) ABSTRACT

A data analysis system includes: a transmission unit receiving research data; a storage unit saving the research data; a control unit generating a research approach, a first parameter, and a second parameter according to an operation instruction; a processing unit obtains research data from to-be-analyzed data by using the transmission unit according to the research approach, and the parameters; the processing unit analyzes the parameters and the research data by using a statistical algorithm, to generate statistical information; and then analyzes the related first parameter, second parameter, and various pieces of research data according to a test algorithm, to generate a statistical test; and a display unit, connected to the processing unit and used to display integration information, where the integration information is obtained by the processing unit by integrating the related first parameter, second parameter, statistical information, and statistical test according to an integration algorithm.

18 Claims, 8 Drawing Sheets

DATA ANALYSIS SYSTEM AND ANALYSIS METHOD THEREFOR

CROSS-REFERENCE TO RELATED APPLICATION

This non-provisional application claims priority under 35 U.S.C. § 119(a) to Patent Application No. 201710312459.9 filed in China, P.R.C. on May 5, 2017, the entire contents of which are hereby incorporated by reference.

BACKGROUND

Technical Field

The present invention relates to a data analysis system, and in particular, to a data analysis system capable of exploring relevance between events in data.

Related Art

In recent years, an issue of big data (big data) is often mentioned, and big data refers to information that involves a huge amount of data and cannot be manually acquired, managed, processed, and arranged within a proper time in a form that can be interpreted by human beings. Therefore, how to process big data and analyze and research the big data and then arrange the big data into information that can be rapidly understood by human beings is a very important subject.

There are multiple analysis methods for big data anecdotally, in which such a method exists: performing searching by using a keyword to obtain data, and then, analyzing related content that corresponds to a particular item and that is in data having a same keyword. That is, data having a same feature is first obtained from big data, and then, a correspondence between the data having the same feature and a particular item is correspondingly analyzed, to obtain an analysis result corresponding to the particular item.

However, if there are different particular items, the foregoing analysis needs to be performed repeatedly, to respectively obtain analysis results that belong to the different particular items, but it is difficult to find out relevance between two different particular items. Therefore, it is necessary to provide a solution, to rapidly analyze different particular items and a relationship between the different particular items.

SUMMARY

In view of the foregoing problem, the present invention provides a data analysis system and an analysis method therefor, so that a user can rapidly understand relevance between different events, to explore various possibilities between the different events.

An embodiment of the present invention provides a data analysis system, including: a transmission unit, a storage unit, a control unit, a processing unit, and a display unit. The transmission unit receives research data. The storage unit stores the research data. The control unit generates a research approach, a first parameter, and a second parameter according to an operation instruction. The processing unit is connected to the transmission unit, the storage unit, and the control unit. The processing unit obtains research data from to-be-analyzed data by using the transmission unit according to the research approach, the first parameter, and the second parameter. The processing unit analyzes the first parameter, the second parameter, and the research data by using a statistical algorithm according to the research approach, to generate statistical information. The processing unit analyzes the related first parameter, second parameter, and various pieces of research data according to a test algorithm, to generate a statistical test. The display unit is connected to the processing unit and used to display integration information. The integration information is obtained by the processing unit by integrating the related first parameter, second parameter, statistical information, and statistical test according to an integration algorithm.

An embodiment of the present invention provides an analysis method for data analysis, including, generating, by a control unit, a first parameter, a second parameter, and a research approach according to an operation instruction; obtaining, from a piece of to-be-analyzed data, at least one piece of research data corresponding to the first parameter and the second parameter; receiving, by a transmission unit, various pieces of research data; analyzing, by a processing unit, the first parameter, the second parameter, and the various pieces of research data by using a statistical algorithm according to the research approach, to generate statistical information; analyzing, by the processing unit, the related first parameter, second parameter, and various pieces of research data according to a test algorithm, to generate a statistical test; integrating, by the processing unit, the first parameter, the second parameter, the statistical information, and the statistical test into integration information according to an integration algorithm; and displaying, by a display unit, the integration information.

According to the foregoing embodiments, in the present invention, a user can rapidly learn of, by using the integration information displayed by the display unit, relevance between the related first parameter and second parameter in the research data. That is, for the research data obtained by the processing unit from the to-be-analyzed data, after analysis and calculation are performed for the related first parameter and second parameter, whether there is high relevance between the corresponding first parameter and second parameter in the research data can be learned of. Therefore, the user can rapidly learn of, by using the integration information, whether the selected first parameter and second parameter have research reference value, so that research efficiency can be improved, and a research result can be improved.

BRIEF DESCRIPTION OF THE DRAWINGS

The present invention will become more fully understood from the detailed description given herein below for illustration only, and thus are not limitative of the present invention, and wherein.

DETAILED DESCRIPTION

Figure 1:
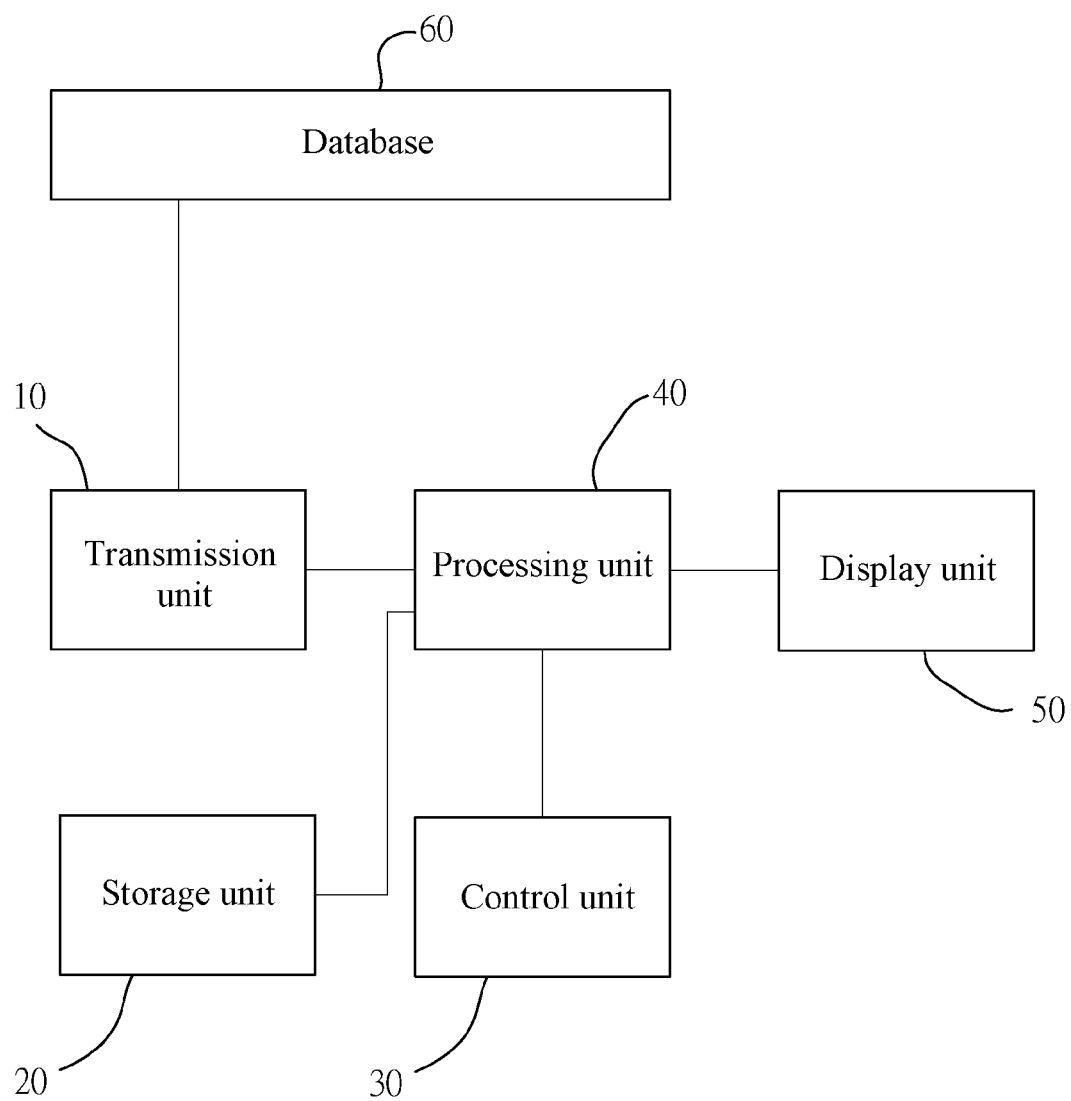
FIG. 1 is a schematic architectural diagram of an event relevance analysis system according to an embodiment of the present invention.
Figure 2:
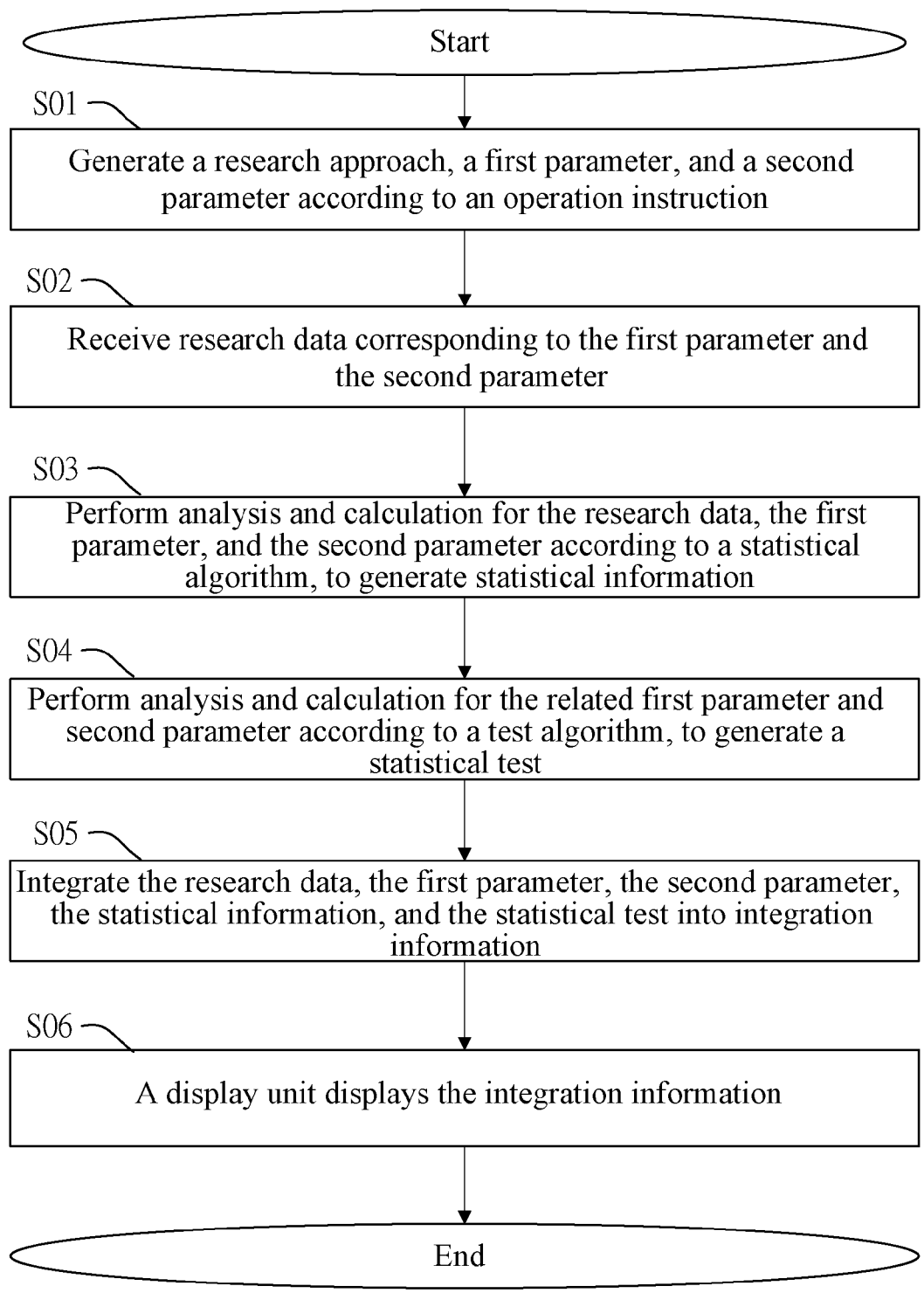
FIG. 2 is a flowchart of an event relevance analysis method according to an embodiment of the present invention.

FIG. 1 is a schematic architectural diagram of an analysis system according to an embodiment of the present invention. FIG. 2 is a flowchart of an analysis method according to an embodiment of the present invention. Referring to FIG. 1 and FIG. 2, an event relevance analysis system in the present invention includes a transmission unit 10, a storage unit 20, a control unit 30, a processing unit 40, and a display unit 50. The processing unit 40 is connected to the transmission unit 10, the storage unit 20, the control unit 30, and the display unit 50.

The transmission unit 10 can receive research data from a database 60. In an embodiment, the transmission unit 10 can receive one or more pieces of research data. The present invention is not limited thereto. In an embodiment, the database 60 stores to-be-analyzed data, and research data is acquired from the to-be-analyzed data and transmitted to the transmission unit 10.

In an embodiment, the transmission unit 10 can be connected to the database 60 in a wired or wireless manner, to obtain the research data from the to-be-analyzed data stored in the database 60.

In an embodiment, the transmission unit 10 can perform transmission by means of WiFi, a GSM, Bluetooth, infrared rays, WiMAX, Zigbee, Zwave, radio frequency (RF), or another wireless transmission manner. Alternatively, the transmission unit 10 can perform transmission by means of the Ethernet, RF232, or another wired transmission manner.

In an embodiment, the database 60 may store big data (Big data). Therefore, a storage unit may exist in the database 60, and may be a read-only memory, a random access memory, a non-persistent memory, a persistent memory, a static memory, a dynamic memory, a flash memory, and/or any device storing digital information.

In an embodiment, in the present invention, multiple databases 60 may exist and may be located in a same equipment room. The present invention is not limited thereto. In some embodiments, various databases 60 may be distributed in different places. In addition, the database 60 may be located in cloud, so that it is convenient to obtain the to-be-analyzed data at any time.

The storage unit 20 stores the research data from the database 60. In an embodiment, the storage unit 20 may be a read-only memory, a random access memory, a non-persistent memory, a persistent memory, a static memory, a dynamic memory, a flash memory, and/or any device storing digital information.

In an embodiment, the database 60 may be integrated with the storage unit 20. That is, after the processing unit 40 transmits a first parameter and a second parameter to the database 60 by using the transmission unit 10, the database 60 immediately obtains corresponding research data from the to-be-analyzed data in the database 60. The research data may be divided into first research data, second research data, or other research data. The present invention is not limited thereto.

The control unit 30 can generate a research approach, a first parameter, and a second parameter according to an operation instruction (that is, step S01 in FIG. 2). In an embodiment, an operation instruction is generated by an operation of a user. That is, the user can deliver the operation instruction by using an operation interface, to select the research approach, a to-be-analyzed cause item (that is, the first parameter), and a to-be-analyzed result item (that is, the second parameter). The operation interface may be displayed on a computer or a handheld device, and then the operation instruction is delivered by using a keyboard or a key or a touch manner. In some embodiments, the operation instruction may also be delivered in a voice manner, that is, the operation instruction is generated by performing voice recognition on a voice of the user.

The display unit 50 receives integration information by using the processing unit 40, and displays the integration information on a display screen. That is, the user can rapidly learn of analysis results of the cause item and the result item by using the display unit 50. Details are provided subsequently.

Herein, after the processing unit 40 receives the research approach, the first parameter, and the second parameter from the control unit 30, the processing unit 40 can be connected to the database 60 by using the transmission unit 10, and receive corresponding research data of the research approach, the first parameter, and the second parameter from the database 60 (that is, step S02), and store the research data in the storage unit 20.

Next, the processing unit 40 performs analysis and calculation for the research data, the first parameter, and the second parameter by using a statistical algorithm according to the research approach, to generate statistical information (that is, step S03), and analyzes the first parameter and the second parameter according to a test algorithm, to generate a statistical test (that is, step S04). Subsequently, the processing unit 40 integrates the first parameter, the second parameter, the statistical information, and the statistical test into integration information according to an integration algorithm (that is, step S05), and transmits the integration information to the display unit 50, so that the display unit 50 displays the integration information (that is, step S06).

In an embodiment, the first parameter and the second parameter of the control unit 30 generally refer to classification conditions, for example, whether it is exposed to styrene (the first parameter) and whether leukemia is got (the second parameter), whether it is in a high temperature region (the first parameter) and whether an ice crusher is bought (the second parameter), whether there is a smoker (the first parameter) and whether lung cancer is got (the second parameter), whether a person has a habit of coffee drinking (the first parameter) and whether there is osteoporosis (the second parameter), or any other classification conditions. The present invention is not limited thereto. That is, the user may select the to-be-analyzed cause item (the first parameter) and the to-be-analyzed result item (the second parameter), to explore relevance between the cause item and the result item.

The integration information displayed by the display unit 50 can display relevance between the first parameter and the second parameter in the research data, so that the user can rapidly understand whether the research data corresponding to the first parameter and the second parameter has research reference value.

In some embodiments, the user can use the control unit 30 to generate a third parameter or a fourth parameter. Analysis and research are performed by using the processing unit 40, to separately explore relevance between the first parameter, the second parameter, the third parameter, and the fourth parameter. In this way, the research data can be rapidly analyzed, to improve research efficiency of a researcher.

In an embodiment, the research approach includes a first research approach, a second research approach, and a third research approach. Detailed content of the first research approach, the second research approach, and the third research approach is described in detail subsequently.

Several embodiments are used below to describe the application of the present invention, but the application of the present invention is not limited to these embodiments.

In a first embodiment, the researcher is intended to research whether occupational exposure to styrene increases a risk of developing leukemia. First, 70,000 employees in 1,000 small and mid-size entities in 1990 to 2012 as research objects (to-be-analyzed data) are already stored in the database 60. Therefore, the researcher (that is, the user) can operate the control unit 30 to select the first research approach, and select the first parameter as whether an employee is occupationally exposed to styrene, and select the second parameter as whether an employee is a patient with leukemia (that is, step S01).

TABLE 1

|  | Second parameter (leukemia) | Relative second parameter (no leukemia) | Total |
|---|---|---|---|
| First parameter (occupational exposure to styrene) | 120 | 29,880 | 30,000 |
| Relative first parameter (no occupational exposure to styrene) | 80 | 39,920 | 40,000 |
| Total | 200 | 69,800 | 70,000 |

Table 1 is a statistical table of the first research approach in the first embodiment. Referring to Table 1, the processing unit 40 receives the first research approach, the first parameter, and the second parameter by using the control unit 30, and can search for and receive, from the database 60 by using the transmission unit 10, research data corresponding to the first research approach, the first parameter, and the second parameter (that is, step S02). In this embodiment, the processing unit 40 can obtain, from the database 60, that there are 120 persons with leukemia (the second parameter) who are occupationally exposed to styrene (the first parameter), and there are 29,880 persons without leukemia who are occupationally exposed to styrene. Similarly, the processing unit 40 can also obtain that there are 80 persons with leukemia who are not occupationally exposed to styrene, and there are 39,920 persons without leukemia who are not occupationally exposed to styrene. In an embodiment, when the processing unit 40 is connected to the database 60 by using the transmission unit 10, the database 60 immediately obtains, from the to-be-analyzed data, research data matching the first research approach, the first parameter, and the second parameter, and then transmits the research data to the processing unit 40 by using the transmission unit 10.

Next, the processing unit 40 can perform analysis and calculation for the foregoing various pieces of research data, first parameter, and second parameter according to a statistical algorithm, to generate statistical information (that is, step S03). The statistical information may be an occurrence rate, an occurrence density, a relative risk, an odds ratio, or another parameter of statistical significance. The present invention is not limited thereto. In some embodiments, the statistical information may be any combination of an occurrence rate, an occurrence density, a relative risk, an odds ratio, and another parameter of statistical significance. That is, the statistical algorithm is a related occurrence rate algorithm, a related occurrence density algorithm, a related relative risk algorithm, a related odds ratio algorithm, or another related algorithm of statistical significance. The present invention is not limited thereto.

Figure 3:
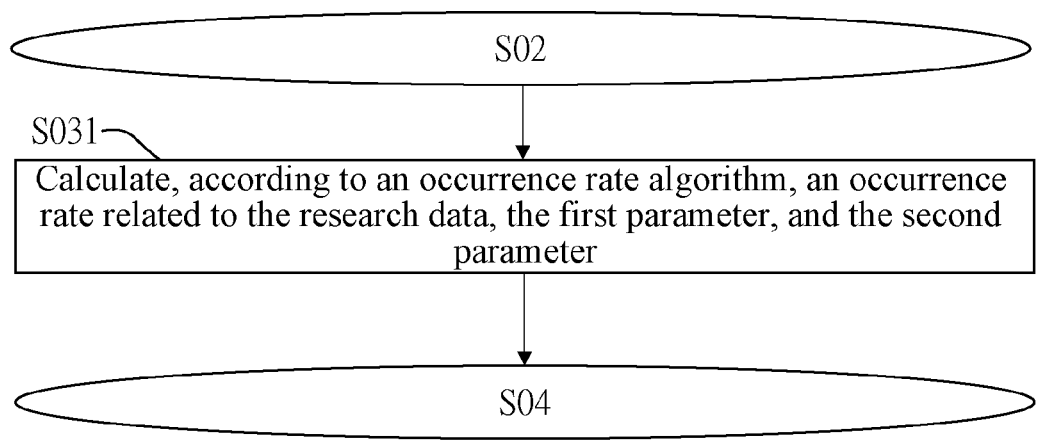
FIG. 3 is a flowchart of calculating an occurrence rate as statistical information according to an embodiment of the present invention.

FIG. 3 is a flowchart of calculating an occurrence rate as statistical information according to an embodiment of the present invention. Referring to FIG. 3, the processing unit 40 calculates, according to the occurrence rate algorithm, an occurrence rate corresponding to the first parameter and the second parameter (that is, step S031). In an embodiment, the occurrence rate algorithm may be (the number of new cases in which a research event occurs/the number of all cases in which the research event possibly occurs)×1000‰, to calculate the occurrence rate.

For example, an occurrence rate for occupational exposure to styrene and leukemia is (120/30,000)×1000‰=4‰, and statistical information thereof is that among every thousand persons who are occupationally exposed to styrene, there are 4 persons who develop leukemia. Similarly, an occurrence rate for no occupational exposure to styrene and leukemia is (80/40,000)×1000‰=2‰, and statistical information thereof is that among every thousand persons who are not occupationally exposed to styrene, there are 2 persons who develop leukemia. In addition, a leukemia occurrence rate of the entire population is (200/70,000)×1000‰=2.86‰, that is, statistical information is that among every thousand persons, there are 2.86 persons who develop leukemia.

Figure 4:
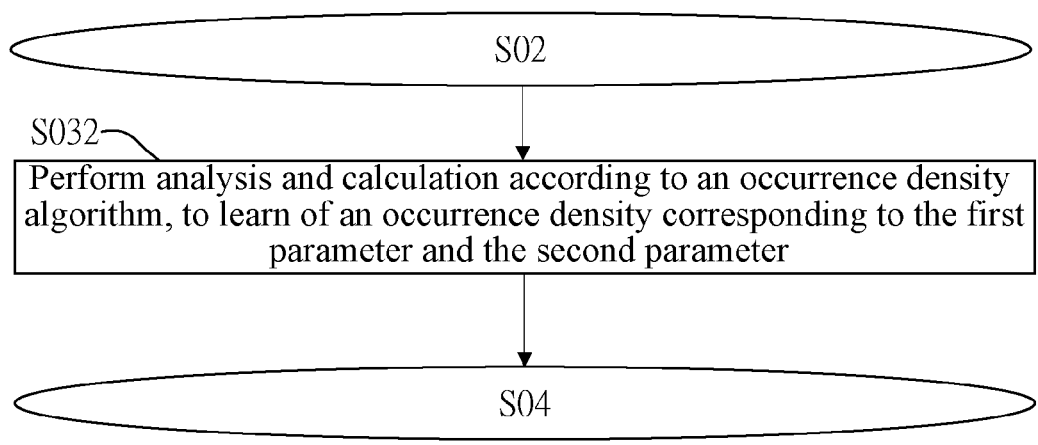
FIG. 4 is a flowchart of calculating an occurrence density as statistical information according to an embodiment of the present invention.

FIG. 4 is a flowchart of calculating an occurrence density as statistical information according to an embodiment of the present invention. Referring to FIG. 4, in an embodiment, the processing unit 40 can further perform analysis and calculation according to the occurrence density algorithm, to learn of an occurrence density corresponding to the first parameter and the second parameter (that is, step S032), and a sum of person-years when there is an event potentially occurring but no event occurring within a period of time (a research period) can be learned of from statistical information obtained by the processing unit 40 through calculation. That is, the number of cases in which an event newly occurs for research objects (groups), a group size, and a time of the case number can be explored accordingly. In this embodiment, that a whole generation is tracked and observed for 23 years (a research period starts from 1990, and tracking is performed until 2012) is stored in the to-be-analyzed data, and if a research case is diagnosed with leukemia, it is considered that an event occurs; otherwise, if the disease is not detected until the end of 2012, it is considered that an event does not occur.

TABLE 2

|  | Event occurring (leukemia) | Event not occurring (no leukemia) | Total | Person-year |
|---|---|---|---|---|
| Exposure to styrene (occupational exposure to styrene) | 120 | 29,880 | 30,000 | 1000,000 |
| No exposure to styrene (no occupational exposure to styrene) | 80 | 39,920 | 40,000 | 1,600,000 |
| Total | 200 | 69,800 | 70,000 | 2,600,000 |

Table 2 is another statistical table of the first research approach in the first embodiment. Referring to Table 2, the processing unit 40 can obtain through calculation according to the foregoing table that an occurrence density of employees with leukemia who are exposed to styrene is (120/1,000,000)×1000=0.12, that is, statistical information indicates that among employees who are exposed to styrene, in every thousand person-years, there is 0.12 person who develops leukemia. Similarly, an occurrence density of employees with leukemia who are not exposed to styrene is (80/1,600,000)×1000=0.05, that is, statistical information is that among employees who are not exposed to styrene, in every thousand person-years, there is 0.05 person who develops leukemia. In addition, a leukemia occurrence density of the entire population is (200/2,600,000)×1000=0.08, that is, statistical information is that in every thousand person-years, there is 0.08 person who develops leukemia.

Figure 5:
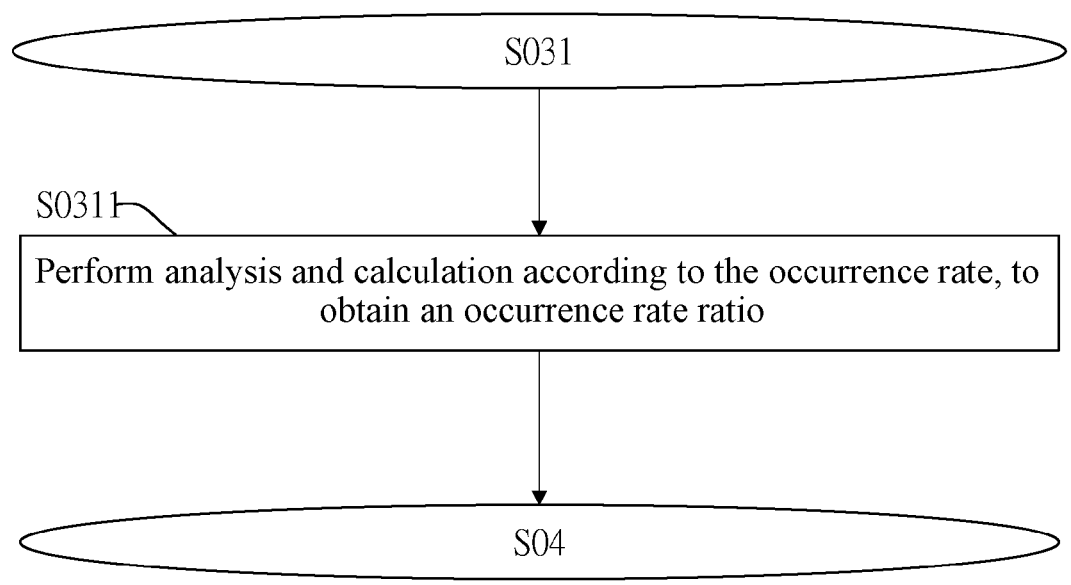
FIG. 5 is a detailed flowchart of an embodiment of step S03 according to the present invention.

FIG. 5 is a detailed flowchart of an embodiment of step S03 according to the present invention. Referring to FIG. 5, in the step of performing, by the processing unit 40, analysis and calculation, to generate statistical information, the processing unit 40 can perform analysis and calculation according to the foregoing various occurrence rates (that is, step S031), to obtain an occurrence rate ratio (that is, step S0311). That is, the occurrence rate for exposure to styrene and leukemia/the occurrence rate for no exposure to styrene and leukemia is 4‰/2‰=2, which indicates that a risk of developing leukemia by a person who is exposed styrene is twice that of developing leukemia by a person who is not exposed to styrene. That is, the processing unit 40 can learn of, according to the occurrence rate, a relative risk (statistical information) of developing leukemia by a person who is exposed to styrene relative to a person who is not exposed to styrene. The occurrence rate ratio is a ratio of an event occurrence rate for exposure to a factor set (group) to an event occurrence rate for no exposure to the factor set (group). That is, in this embodiment, the occurrence rate ratio is a ratio of an event occurrence rate for exposure to styrene to an event occurrence rate for no exposure to styrene.

Figure 6:
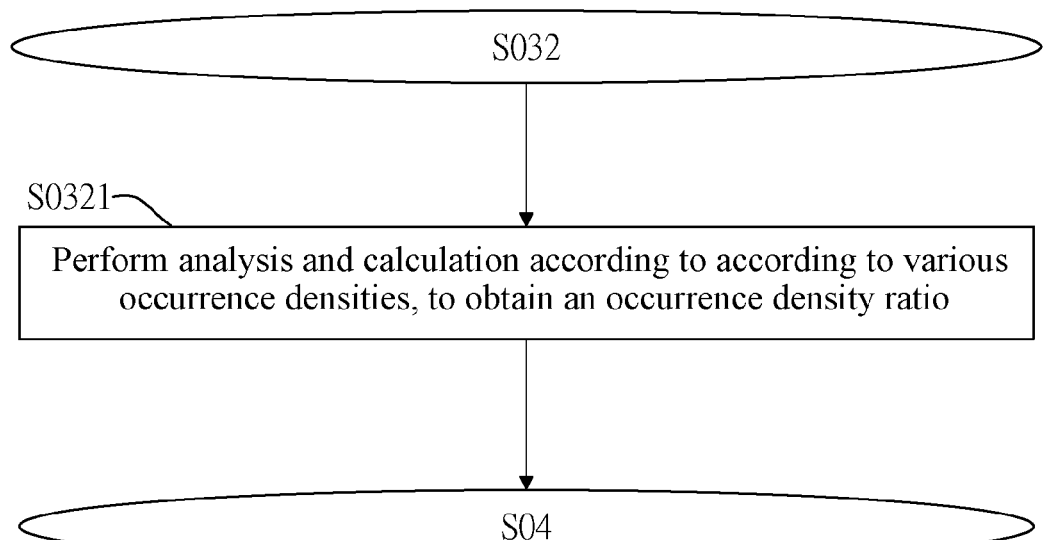
FIG. 6 is a detailed flowchart of another embodiment of step S03 according to the present invention.

FIG. 6 is a detailed flowchart of another embodiment of step S03 according to the present invention. Referring to FIG. 6, in an embodiment, in the step of performing, by the processing unit 40, analysis and calculation, to generate statistical information, an occurrence density ratio can be obtained by performing analysis and calculation according to the foregoing various occurrence densities (that is, step S032) (that is, step S0321). That is, the occurrence density for exposure to styrene and leukemia/the occurrence density for no exposure to styrene and leukemia is 0.12/0.05=2.4, which indicates that an occurrence density of developing leukemia by a person who is exposed styrene is 2.4 times that of developing leukemia by a person who is not exposed to styrene. That is, an occurrence density of developing leukemia by a person who is exposed styrene is 2.4 times that of developing leukemia by a person who is not exposed to styrene. The occurrence density ratio is a ratio of an event occurrence density for exposure to a factor set (group) to an event occurrence density for no exposure to the factor set (group). That is, in this embodiment, the occurrence density ratio is a ratio of an event occurrence density for exposure to styrene to an event occurrence density for no exposure to styrene.

Figure 7:
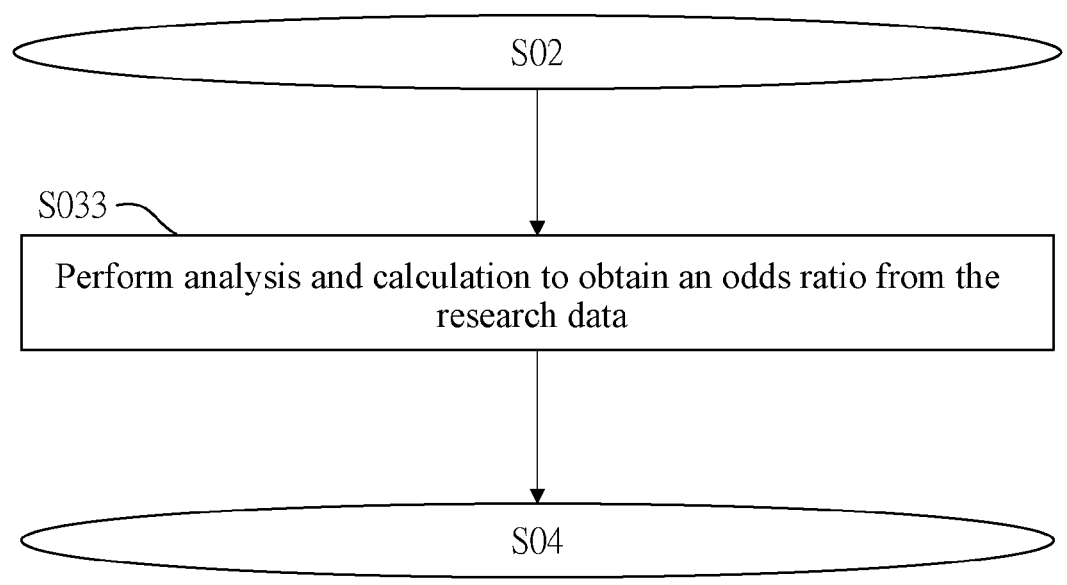
FIG. 7 is a detailed flowchart of still another embodiment of step S03 according to the present invention.

FIG. 7 is a detailed flowchart of still another embodiment of step S03 according to the present invention. Referring to FIG. 7, in an embodiment, the processing unit 40 can perform analysis and calculation according to the odds ratio algorithm, to learn of an odds ratio (statistical information) corresponding to the first parameter and the second parameter (that is, step S033), which is that, the processing unit 40 can obtain, according to the foregoing descriptions, a ratio of event occurrence odds for exposure to a factor set (group) to event occurrence odds for no exposure to the factor set (group). That is, a ratio of a result obtained by dividing an occurrence number of persons with leukemia who are exposed to styrene by a non-occurrence number to a result obtained by dividing an occurrence number of persons with leukemia who are not exposed to styrene by a non-occurrence number is the odds ratio ((120/29,880)/(80/39,920)=2), and statistical information thereof indicates that odds of developing leukemia by a person who is exposed to styrene are twice that of developing leukemia by a person who is not exposed to styrene. That is, the researcher voluntarily selects a type or a combination of statistical information according to a requirement, to perform analysis and determining. The present invention is not limited thereto.

In an embodiment, referring to FIG. 2 again, the processing unit 40 can perform analysis and calculation according to a test algorithm, to obtain a statistical test corresponding to the first parameter and the second parameter (that is, step S04). The statistical test is relevance and a causal relationship between the first parameter and the second parameter. That is, based on the statistical test obtained by the processing unit 40 by performing analysis and calculation by using the test algorithm, the relevance and the causal relationship between the first parameter and the second parameter can be derived in the research data.

The test algorithm includes one or any combination of a statistical hypothesis testing algorithm, a single-factor/multiple-factor analysis algorithm, and another related test algorithm. The present invention is not limited thereto.

In an embodiment, the statistical hypothesis testing algorithm includes one of a Chi-square test algorithm (Chi-Square test), a Fisher exact test algorithm (Fisher exact test), an independent two-sample T-test algorithm (Two-sample T-test), and a Wilcoxon rank-sum test algorithm (Wilcoxon rank-sum test).

The Chi-square test algorithm is to explore whether there is relevance between two categorical variables (categorical variables), and test only relevance between the two instead of indicating a causal relationship between the two.

The Fisher exact test algorithm is to test relevance between two categorical variables, and is applicable to a problem of relevance testing in a 2×2 contingency table. The method is considering all random arrangements directly according to a probability theory provided by data, to calculate an occurrence probability of an observed sample number when two variables are independent and irrelevant.

The independent two-sample T-test algorithm is to explore a difference between population means (whether it is greater than, less than, or equal to a particular value) between continuous variables (continuous variables) in two independent groups of samples, that is, compare to determine a difference between two groups of continuous variables.

In the Wilcoxon rank-sum test algorithm, when distribution of two groups of continuous variables is not normal, and a sample number is excessively small or there is an extreme value, medians are used as measures of central tendency for the two groups, that is, a Wilcoxon rank-sum test may be used to compare to determine whether there is a difference between the medians in the two groups.

TABLE 3

| Item | | Case number (%) | | p-value |
|---|---|---|---|---|
| | | Exposure to styrene (occupational exposure to styrene) (n = 200) | No exposure to styrene (no occupational exposure to styrene) (n = 69,800) | |
| Gender | Male | 105 (52.5) | 35,000 (50.1) | 0.08[a] |
| | Female | 95 (47.5) | 34,800 (49.9) | |
| Age M ± SD | | 40.50 ± 10.45 | 45.30 ± 8.55 | 0.03[b] |
| Habit of cigarette smoking | Yes | 70 (35.0) | 28,000 (40.1) | 0.04[a] |
| | No | 130 (65.0) | 41,800 (59.9) | |
| Habit of alcohol drinking | Group of high alcohol consumption | 90 (45.0) | 30,500 (43.7) | 0.04[a] |
| | Group of low alcohol consumption | 110 (55.0) | 39,300 (56.3) | |
| Family medical history | Yes | 85 (42.5) | 33,800 (48.4) | 0.72[a] |
| | No | 115 (57.5) | 36,000 (41.6) | |

Table 3 is a descriptive and inferential statistical table corresponding to the first research approach in the first embodiment. Referring to Table 3, in descriptive statistics, distribution of data of continuous variables is presented by using an average value and a standard deviation, and distribution of data of categorical variables is presented by using a case number and a percentage. In inferential statistics, a difference between average values of ages of persons exposed and not exposed to styrene is explored by using a T-test, and whether there is relevance between whether it is exposed to styrene and other attribute factors than an age is explored by using a Chi-square test. Therefore, it may be learned from Table 3 that, there is a statistically significant difference or significant relevance between distribution of ages, habits of cigarette smoking, and habits of alcohol drinking in exposure and no exposure to styrene (that is, when p<0.05, there is significant relevance between a corresponding item and the first parameter, and a value of p is calculated and learned of according to the statistical hypothesis testing algorithm). An annotation a in the p-value field is obtained according to the Chi-square test algorithm. An annotation b in the p-value field is obtained according to the T-test algorithm. A level of significance is 5%.

In an embodiment, the single-factor/multiple-factor analysis algorithm includes one of a survival analysis (Survival Analysis) algorithm, a Cox proportional hazards model (Cox Proportional Hazards Model) algorithm, a Poisson regression model (Poisson Regression Model) algorithm, a logistic regression model (Logistic Regression Model) algorithm, and another correlation factor analysis algorithm. The present invention is not limited thereto.

TABLE 4

| Item | | Coefficient estimated value | Indicator of estimated value Hazard ratio (HR) (95% CI) | p-value |
|---|---|---|---|---|
| Single-factor analysis | | | | |
| Gender | Male | 0.032 | 1.055 (0.955, 1.108) | 0.111 |
| | Female | | | |
| Age | | 0.113 | 1.507 (1.415, 1.751) | 0.222 |
| Habit of cigarette smoking | Yes | 0.555 | 2.339 (1.946, 2.458) | 0.028 |
| | No | | | |
| Habit of alcohol drinking | Group of high alcohol consumption | 0.677 | 2.314 (1.998, 2.569) | 0.206 |
| | Group of low alcohol consumption | | | |
| Family medical history | Yes | 0.279 | 1.666 (1.433, 1.768) | 0.154 |
| | No | | | |
| Exposure to styrene | Yes | 0.484 | 1.758 (1.208, 1.901) | 0.044 |
| | No | | | |
| Multiple-factor analysis | | | | |
| Gender | Male | 0.029 | 1.085 (1.055, 1.098) | 0.218 |
| | Female | | | |
| Age | | 0.206 | 1.758 (0.806, 1.964) | 0.121 |
| Habit of cigarette smoking | Yes | 0.584 | 2.328 (0.845, 2.458) | 0.135 |
| | No | | | |
| Habit of alcohol drinking | Group of high alcohol consumption | 0.846 | 2.561 (1.448, 2.759) | 0.102 |
| | Group of low alcohol consumption | | | |
| Family medical history | Yes | 0.148 | 1.507 (0.415, 1.751) | 0.254 |
| | No | | | |
| Exposure to styrene | Yes | 0.021 | 1.263 (0.985, 2.651) | 0.024 |
| | No | | | |

Table 4 shows Cox regression analysis results in the first embodiment. Referring to Table 4, results obtained according to the single-factor analysis algorithm show that, a habit of cigarette smoking and exposure to styrene are both statistically related to developing leukemia (p<0.05). Results obtained according to the multiple-factor analysis algorithm show that, only exposure to styrene is a significant hazardous factor for developing leukemia, and there is statistical relevance between the two (p<0.05), that is, a risk of developing leukemia by a person who is exposed to styrene is 1.263 times that of developing leukemia by a person who is not exposed to styrene. That is, a risk of developing leukemia by a person who is exposed to styrene is increased by 26.3%, and an upper limit of a confidence interval of the hazard ratio shows that a risk may be increased to 165.1%.

TABLE 5

| Item | Coefficient estimated value (95% CI) | p-value |
|---|---|---|
| Up to the age of 49 | −5.863 (−7.603, −4.927) | 0.101 |
| The age from 50 to 59 | 1.847 (1.387, 2.316) | 0.081 |
| The age of 60 and more | 1.325 (0.835, 1.716) | 0.042 |

Table 5 shows Poisson regression results of leukemia occurrence rates and ages in the first embodiment. Referring to Table 5, ages are divided into three age groups: up to the age of 49, the age from 50 to 59, and the age of 60 and more in Table 5. A leukemia occurrence rate in every person-year (a year per person) for a basal age group (up to the age of 49) is estimated to be $e^{\beta_0}=e^{-5.863}=0.003$. Leukemia occurrence rates in every person-year for age groups of the age from 50 to 59 and the age of 60 and more are respectively estimated to be $e^{-5.863+1.847}=0.018$ and $e^{-5.863+1.325}=0.011$. Compared with the basal age group (up to the age of 49), leukemia occurrence rate ratio values (IRR) in every person-year for the age groups are respectively 6.341 and 3.762. Therefore, it may be learned from Table 5 that, the age group of the age of 60 and more is significantly related to a leukemia occurrence rate ($p<0.05$).

TABLE 6

| Item | | Coefficient estimated value | Odds ratio (OR) (95% CI) | p-value |
|---|---|---|---|---|
| Single-factor analysis | | | | |
| Gender | Male | 0.496 | 1.791 (1.563, 2.008) | 0.069 |
| | Female | | | |
| Age | | 0.077 | 1.151 (0.933, 1.357) | 0.042 |
| Habit of cigarette smoking | Yes | 0.678 | 2.534 (1.937, 2.747) | 0.022 |
| | No | | | |
| Habit of alcohol drinking | Group of high alcohol consumption | 0.438 | 1.693 (1.345, 1.998) | 0.083 |
| | Group of low alcohol consumption | | | |
| Family medical history | Yes | 0.069 | 1.136 (0.508, 1.201) | 0.133 |
| | No | | | |
| Exposure to styrene | Yes | 0.214 | 1.239 (0.999, 1.351) | 0.029 |
| | No | | | |
| Multiple-factor analysis | | | | |
| Gender | Male | 0.529 | 2.184 (1.515, 2.298) | 0.138 |
| | Female | | | |
| Age | | 0.196 | 1.355 (0.956, 1.356) | 0.062 |
| Habit of cigarette smoking | Yes | 0.854 | 2.785 (2.995, 2.956) | 0.125 |
| | No | | | |
| Habit of alcohol drinking | Group of high alcohol consumption | 0.514 | 2.158 (2.045, 2.365) | 0.091 |
| | Group of low alcohol consumption | | | |
| Family medical history | Yes | 0.158 | 1.141 (0.805, 1.155) | 0.125 |
| | No | | | |
| Exposure to styrene | Yes | 0.365 | 1.696 (0.987, 2.007) | 0.035 |
| | No | | | |

Table 6 is a statistical table of logistic regression results of leukemia related hazardous factors in the first embodiment. Referring to Table 6, results obtained according to the single-factor analysis algorithm show that, an age, a habit of cigarette smoking, and exposure to styrene are all statistically related to developing leukemia ($p<0.05$). However, results obtained according to the multiple-factor analysis algorithm show that, only exposure to styrene is a significant hazardous factor for developing leukemia, and there is statistical relevance between the two ($p<0.05$), and odds of developing leukemia by a person who is exposed to styrene are 1.696 times that of developing leukemia by a person who is not exposed to styrene. That is, odds of developing leukemia by a person who is exposed to styrene are increased by 69.6%, and an upper limit of a confidence interval of the odds ratio shows that the odds may be increased to 100.7%.

Figure 8:
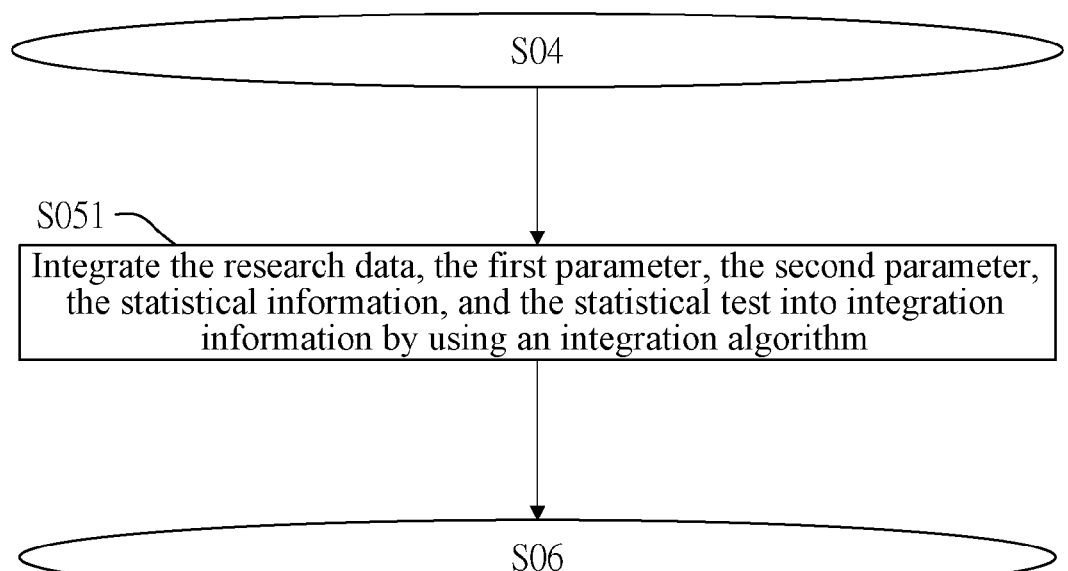
FIG. 8 is a detailed flowchart of step S05 according to the present invention.

FIG. 8 is a detailed flowchart of step S05 according to the present invention. Table 7 is an exemplary table of the integration information in the first embodiment of the present invention. Referring to FIG. 8 and Table 7, the processing unit 40 integrates the foregoing first parameter, second parameter, statistical information, and statistical test into the integration information by using the integration algorithm (that is, step S051), and transmits the integration information to the display unit 50 for display. In an embodiment, in the integration algorithm, a text, a data, a table, or the like may be properly added according to a result of the first parameter, the second parameter, the statistical information, and the statistical test, to be used as an auxiliary description. For example, in the integration information, the foregoing various occurrence rates (a leukemia occurrence rate of a person who is exposed=4‰, that is, among every thousand persons who are occupationally exposed to styrene, there are 4 persons who develop leukemia; a leukemia occurrence rate of a person who is not exposed=2‰, that is, among every thousand persons who are not occupationally exposed to styrene, there are 2 persons who develop leukemia; and a leukemia occurrence rate of the entire population=2.86‰, that is, among every thousand persons, there are 2.86 persons who develop leukemia), various pieces of statistical information (an occurrence rate ratio=2, indicating that a risk of developing leukemia by a person who is exposed to styrene is twice that of developing leukemia by a person who is not exposed to styrene, that is, a risk of developing leukemia by a person who is exposed is twice that of developing leukemia by a person who is not exposed; and an odds ratio=2, indicating that odds of developing leukemia by a person who is exposed to styrene are twice that of a person who is not exposed to styrene), and various statistical tests (there is a statistically significant difference or significant relevance between distribution of ages, habits of cigarette smoking, and habits of alcohol drinking in exposure and no exposure to styrene ($p<0.05$), and the single-factor/multiple-factor analysis (the survival analysis, the Poisson regression model, or the logistic regression model)) are displayed. Therefore, the integration information may be combined with table information or a text description corresponding to the first parameter and the second parameter by using the integration algorithm, to be rapidly understood by the researcher, and further, a research result can be easily understood by the general population without related professional knowledge.

TABLE 7

1. Occurrence rate
    1. A leukemia occurrence rate of a person who is exposed = 4‰, that is, among every thousand persons who are occupationally exposed to styrene, there are 4 persons who develop leukemia.
    2. A leukemia occurrence rate of a person who is not exposed = 2‰, that is, among every thousand persons who are not occupationally exposed to styrene, there are 2 persons who develop leukemia.
    3. A leukemia occurrence rate of the entire population = 2.86‰, that is, among every thousand persons, there are 2.86 persons who develop leukemia.

TABLE 7-continued

2. Statistical information
   1. Relative risk (hazard) ((Relative Risk, RR), and risk(hazard) ratio (Risk Ratio, RR)
      An occurrence rate ratio = 2, indicating that a risk of developing leukemia by a person who is exposed to styrene is twice that of developing leukemia by a person who is not exposed to styrene, that is, a risk of developing leukemia by a person who is exposed is twice that of developing leukemia by a person who is not exposed.
   2. Odds ratio (Odds Ratio, OR), and ratio of two odds (Ratio of two Odds)
      An odds ratio = 2, indicating that odds of developing leukemia by a person who is exposed to styrene are twice that of developing leukemia by a person who is not exposed to styrene.
3. Statistical test
      There is a statistically significant difference or significant relevance between distribution of ages, habits of cigarette smoking, and habits of alcohol drinking in exposure and no exposure to styrene (p < 0.05).
4. Single-factor/multiple-factor analysis
   1. Survival analysis: Cox proportional hazards model (Cox Proportional Hazards Model)
      Results obtained from the single-factor analysis show that, a habit of cigarette smoking and exposure to styrene are both statistically related to developing leukemia (p < 0.05). Results obtained from the multiple-factor analysis show that, only exposure to styrene is a significant hazardous factor for developing leukemia, and there is statistical relevance between the two (p < 0.05), and a risk of developing leukemia by a person who is exposed to styrene is 1.263 times that of developing leukemia by a person who is not exposed to styrene. That is, a risk of developing leukemia by a person who is exposed to styrene is increased by 26.3%, and an upper limit of a confidence interval of the hazard ratio shows that a risk may be increased up to 165.1%.
   2. Poisson regression model (Poisson Regression Model)
      The age group of the age of 60 and more is significantly related to a leukemia occurrence rate (p < 0.05).
   3. Logistic regression model (Logistic Regression Model)
      Results obtained from the single-factor analysis show that, an age, a habit of cigarette smoking and exposure to styrene are both statistically related to developing leukemia (p < 0.05). Results obtained from the multiple-factor analysis show that, there is statistical relevance between only exposure to styrene and developing leukemia (p < 0.05), that is, odds of developing leukemia by a person who is exposed to styrene are 1.696 times that of developing leukemia by a person who is not exposed to styrene. That is, odds of developing leukemia by a person who is exposed to styrene is increased by 69.6%, and an upper limit of a confidence interval of the odds ratio shows that the odds may be increased up to 100.7%.

In a second embodiment, similar to the first embodiment, the researcher is intended to use the second research approach to research whether occupational exposure to styrene (the first parameter) increases a risk of developing leukemia (the second parameter). Therefore, 70,000 employees in 1,000 small and mid-size entities in 1990 to 2012 as research objects (to-be-analyzed data) are already stored in the database 60. The first parameter is whether an employee is occupationally exposed to styrene (that is, step S01), and the second parameter is selected as whether an employee is a patient with leukemia (that is, step S01), and the second research approach is selected. In this embodiment, the research data obtained by the processing unit 40 from the database 60 is divided into first research data and second research data (that is, step S02). In the first research data, 200 employees who are proved by means of pathologic examination to be patients newly diagnosed with leukemia in 1990 to 2012 are selected as a case study group, and 500 employees who are not patients with leukemia in the same database within the same period in 1990 to 2012 are selected as a control group. In the second research data, 200 employees who are proved by means of pathologic examination to be patients newly diagnosed with leukemia in 1990 to 2012 are selected as a case study group. By means of 1:1 paring, 200 employees having same genders as cases, having a no more than 2-year age gap from the cases, and excluding non-cases of persons having other malignant tumors are selected as a control group, and there are 200 pairs in total. Therefore, content of various pieces of research data in the first research approach is different from content of various pieces of research data obtained from the second research approach.

Table 8 is a statistical table related to the first research data in the second research approach in the second embodiment of the present invention. Table 9 is a statistical table of the second research data in the second research approach in the second embodiment of the present invention. Referring to Table 8 and Table 9, the processing unit 40 can separately perform calculation according to a statistical algorithm, to obtain statistical information of the first data and the second data (that is, step S03). In this embodiment, the processing unit 40 can separately calculate an exposure rate for the first research data and the second research data by using an exposure algorithm.

TABLE 8

| | Case study group (leukemia) | Control group (no leukemia) | Total |
|---|---|---|---|
| Exposure to styrene (occupational exposure to styrene) | 120 | 100 | 220 |

TABLE 8-continued

|  | Case study group (leukemia) | Control group (no leukemia) | Total |
|---|---|---|---|
| No exposure to styrene (no occupational exposure to styrene) | 80 | 400 | 480 |
| Total | 200 | 500 | 700 |

Therefore, it may be learned from Table 8 that, an exposure rate of the case study group in the first research data=(120/200)×100%=60%, that is, among the 200 patients with leukemia, there are 120 persons who are exposed to styrene, and the exposure rate is 60%. An exposure rate of the control group in the first research data=(100/500)×100%, that is, 20%, that is, among the 500 persons without leukemia, there are 100 persons who are exposed to styrene, and the exposure rate is 20%.

TABLE 9

|  | Control group (no leukemia) | | |
|---|---|---|---|
| Case study group (leukemia) | Exposure to styrene (occupational exposure to styrene) | No exposure to styrene (no occupational exposure to styrene) | Total |
| Exposure to styrene (occupational exposure to styrene) | 30 | 100 | 130 |
| No exposure to styrene (no occupational exposure to styrene) | 50 | 20 | 70 |
| Total | 80 | 120 | 200 |

Therefore, it may be learned from Table 9 that, an exposure rate of the case study group in the second research data=(130/200)×100%=65%, that is, among the 200 patients with leukemia, there are 130 persons who are exposed to styrene, and the exposure rate is 65%. An exposure rate of the control group in the second research data=(80/200)× 100%=40%, that is, among the 200 persons without leukemia, there are 80 persons who are exposed to styrene, and the exposure rate is 40%.

Next, the processing unit 40 can continue to perform analysis according to the second research approach, the first research data, the second research data, the first parameter, and the second parameter, to generate statistical information (that is, step S03). For example, an odds ratio (statistical information) in the first research data=(120*400)/(100*80) =6, indicating that exposure odds for leukemia are 6 times that for no leukemia, that is, odds of being exposed to styrene by a person with leukemia are 6 times that of being exposed to styrene by a person without leukemia. An odds ratio (statistical information) in the second research data=100/50=2, indicating that exposure odds for leukemia are twice that for no leukemia, that is, odds of being exposed to styrene by a person with leukemia are twice that of being exposed to styrene by a person without leukemia. The statistical information is generated in a manner similar to that in the descriptions of the first embodiment, and details are not described herein again.

Table 10 is a descriptive and inferential statistical table corresponding to the second research approach in the second embodiment. The processing unit 40 separately performs analysis according to a test algorithm, to obtain statistical tests that separately correspond to the second parameter and that are in the first research data and the second research data. That is, based on the statistical tests obtained by the processing unit 40 by performing analysis and calculation by using the test algorithm, relevance between the first research data and the second research data corresponding to the second parameter can be derived.

TABLE 10

|  |  | Case number (%) | | |
|---|---|---|---|---|
| Item | | Case study group (leukemia) (n = 200) | Control group (no leukemia) (n = 500) | p-value |
| Gender | Male | 99 (49.5) | 200 (40.0) | 0.11 [a] |
|  | Female | 101 (50.5) | 300 (60.0) |  |
| Age M ± SD |  | 42.51 ± 8.63 | 38.38 ± 10.55 | 0.04 [b] |
| Habit of cigarette smoking | Yes | 95 (47.5) | 230 (46.0) | 0.03 [a] |
|  | No | 105 (52.5) | 270 (54.0) |  |
| Habit of alcohol drinking | Group of high alcohol consumption | 90 (45.0) | 180 (36.0) | 0.09 [a] |
|  | Group of low alcohol consumption | 110 (55.0) | 320 (64.0) |  |
| Family medical history | Yes | 85 (42.5) | 190 (38.0) | 0.83 [a] |
|  | No | 115 (57.5) | 310 (62.0) |  |

Referring to Table 10, in descriptive statistics, distribution of data of continuous variables is presented by using an average value and a standard deviation, and distribution of data of categorical variables is presented by using a case number and a percentage. In inferential statistics, a difference between average values of ages of the case study group and the control group is explored by using a T-test, and whether there is relevance between whether there is leukemia and other attribute factors than an age is explored by using the Chi-square test algorithm. Therefore, it may be learned from Table 10 that, there is a statistically significant difference or significant relevance between distribution of ages and habits of cigarette smoking in leukemia and no leukemia ($p<0.05$). An annotation a in the p-value field is obtained according to the Chi-square test algorithm. An annotation b in the p-value field is obtained according to the T-test algorithm. A level of significance is 5%.

TABLE 11

|  |  | Case number (%) | | |
|---|---|---|---|---|
| Item | | Case study group (leukemia) (n = 200) | Control group (no leukemia) (n = 200) | p-value |
| Gender | Male | 99 (49.5) | 100 (50.0) | 0.12 [a] |
|  | Female | 101 (50.5) | 100 (50.0) |  |
| Age M ± SD |  | 42.51 ± 8.63 | 40.98 ± 10.53 | 0.02 [b] |
| Habit of cigarette smoking | Yes | 95 (47.5) | 90 (45.0) | 0.04 [a] |
|  | No | 105 (52.5) | 110 (55.0) |  |
| Habit of alcohol drinking | Group of high alcohol consumption | 90 (45.0) | 80 (40.0) | 0.11 [a] |
|  | Group of low alcohol consumption | 110 (55.0) | 120 (60.0) |  |

TABLE 11-continued

|  |  | Case number (%) | | |
|---|---|---|---|---|
|  |  | Case study group (leukemia) (n = 200) | Control group (no leukemia) (n = 200) | p-value |
| Family medical history | Yes | 85 (42.5) | 95 (47.5) | 0.94 [a] |
|  | No | 115 (57.5) | 105 (52.5) |  |

Table 11 is another descriptive and inferential statistical table corresponding to the second research approach in the second embodiment. Referring to Table 11, in descriptive statistics, distribution of data of continuous variables is presented by using an average value and a standard deviation, and distribution of data of categorical variables is presented by using a case number and a percentage. In inferential statistics, a difference between average values of ages of the case study group and the control group is explored by using a T-test, and whether there is relevance between whether there is leukemia and other attribute factors than an age is explored by using the Chi-square test algorithm. Therefore, it may be learned from Table 11 that, there is a statistically significant difference or significant relevance between distribution of ages and habits of cigarette smoking in leukemia and no leukemia (p<0.05). An annotation a in the p-value field is obtained according to the Chi-square test algorithm. An annotation b in the p-value field is obtained according to the T-test algorithm. A level of significance is 5%.

Next, the processing unit 40 can also perform analysis and calculation according to the single-factor/multiple-factor analysis algorithm, to understand statistical relevance.

For example, results obtained according to the single-factor analysis algorithm for the first research data show that, an age, a habit of cigarette smoking, and exposure to styrene are all statistically related to developing leukemia (p<0.05). Results obtained according to the multiple-factor analysis algorithm show that, there is statistical relevance between an age and exposure to styrene and developing leukemia (p<0.05). Therefore, in the first research data, as an age increases annually, odds of developing leukemia are increased by 67.5%, and odds of developing leukemia by a person who is exposed to styrene are 1.364 times that of developing leukemia by a person who is not exposed to styrene. That is, odds of developing leukemia by a person who is exposed to styrene are increased by 36.4%, and an upper limit of a confidence interval of the odds ratio shows that the odds may be increased up to 116.3%.

In addition, results obtained according to the single-factor analysis algorithm for the second research data show that, a gender, a habit of cigarette smoking, and exposure to styrene are all statistically related to developing leukemia (p<0.05). Results obtained according to the multiple-factor analysis algorithm show that, there is statistical relevance between only exposure to styrene and developing leukemia (p<0.05). Therefore, in the second research data, odds of developing leukemia by a person who is exposed to styrene are 2.764 times that of developing leukemia by a person who is not exposed to styrene. That is, odds of developing leukemia by a person who is exposed to styrene are increased by 176.4%, and an upper limit of a confidence interval of the odds ratio shows that the odds may be increased up to 200.6%.

Herein, the processing unit 40 integrates the foregoing first parameter, second parameter, various pieces of statistical information, and various statistical tests into integration information (similar to Table 7 in the first embodiment, and a display result thereof may be determined according to an actual requirement) by using the integration algorithm, and transmits the integration information to the display unit 50 for display. That is, in the integration information, the foregoing various pieces of statistical information and various statistical tests are displayed. In addition, the integration information may be combined with table information or a text description corresponding to the first parameter and the second parameter, to be rapidly understood by the researcher, and further, a research result can be easily understood by the general population without related professional knowledge.

In a third embodiment, similar to the first and second embodiments, the researcher is intended to use the third research approach to research whether occupational exposure to styrene (the first parameter) increases a risk of developing leukemia (the second parameter) (that is, step S01). In third research data, 200 employees who are proved by means of pathologic examination to be patients newly diagnosed with leukemia in 1990 to 2012 are selected as a case study group (that is, step S02). 500 employees who are not patients with leukemia in the same database within the same period are selected as a control group (that is, step S02). In fourth research data, 200 employees who are proved by means of pathologic examination to be patients newly diagnosed with leukemia in 1990 to 2012 in an occupational health survey database are selected as a case study group (that is, step S02). By means of 1:1 paring, 200 employees having same genders as cases, having a no more than 2-year age gap from the cases, and excluding non-cases of persons having other malignant tumors are selected as a control group, and there are 200 pairs in total (that is, step S02). Therefore, the third research data and the fourth research data in the third research approach are different from the various pieces of research data in the first research approach and the various pieces of research data in the second research approach.

Table 12 is a statistical table related to the third research data in the third research approach in the third embodiment. Referring to Table 12, in the third research data, during observation for 23 years (a research period starts from 1990, and tracking is performed until 2012), if a research case is diagnosed with leukemia, it is considered that an event occurs; otherwise, if the disease is not detected until the end of 2012, it is considered that an event does not occur.

TABLE 12

|  | Case study group (leukemia) | Control group (no leukemia) | Total | Person-year |
|---|---|---|---|---|
| Exposure to styrene (occupational exposure to styrene) | 130 | 220 | 350 | 20,000 |
| No exposure to styrene (no occupational exposure to styrene) | 70 | 280 | 350 | 22,000 |
| Total | 200 | 500 | 700 | 42,000 |

According to the third research data, the processing unit 40 can obtain through calculation according to a statistical algorithm (such as the occurrence rate algorithm) that a leukemia occurrence rate=(200/700)×1000‰ o=285.71‰ (that is, step S03), indicating that among every thousand persons, there are 285.71 persons who develop leukemia. In addition, in an embodiment, the processing unit 40 can also obtain through calculation according to a statistical algorithm (such as the occurrence density algorithm) that a leukemia occurrence density=(200/42,000)×1000=4.76 (that is, step S032), indicating that among every thousand persons, there are 4.76 persons who develop leukemia.

TABLE 13

| Case study group (leukemia) | Control group (no leukemia) | | |
|---|---|---|---|
| | Exposure to styrene (occupational exposure to styrene) | No exposure to styrene (no occupational exposure to styrene) | Total |
| Exposure to styrene (occupational exposure to styrene) | 40 | 110 | 150 |
| No exposure to styrene (no occupational exposure to styrene) | 30 | 20 | 50 |
| Total | 70 | 130 | 200 |

Table 13 is a statistical table related to the fourth research data in the third research approach in the third embodiment. Similarly, the processing unit 40 can also obtain through calculation according to the occurrence rate algorithm that a leukemia occurrence rate=(200/400)×1000‰=500‰ (that is, step S031), that is, among every thousand persons, there are 500 persons who develop leukemia.

That is, the processing unit 40 can separately perform analysis and calculation according to a statistical algorithm, to obtain statistical information in the third research data and the fourth research data (that is, step S03). For example, in this embodiment, the processing unit 40 may further calculate odds ratios in the third research data and the fourth research data according to the odds ratio algorithm. For example, the odds ratio in the third research data may be (130*280)/(220*70)=2.36, indicating that exposure odds for leukemia are 2.36 times that for no leukemia, that is, odds of being exposed to styrene by a person with leukemia are 2.36 times that of being exposed to styrene by a person without leukemia. In addition, the odds ratio in the fourth research data may be 110/30=3.67, indicating that exposure odds for leukemia are 3.67 times that for no leukemia, that is, odds of being exposed to styrene by a person with leukemia are 3.67 times that of being exposed to styrene by a person without leukemia. Statistical information of another type (such as a relative risk or others) is not described in detail herein.

TABLE 14

| Item | | Case study group (leukemia) (n = 200) | Control group (no leukemia) (n = 500) | p-value |
|---|---|---|---|---|
| Gender | Male | 100 (50.0) | 200 (40.0) | 0.09 [a] |
| | Female | 100 (50.0) | 300 (60.0) | |

TABLE 14-continued

| Item | | Case study group (leukemia) (n = 200) | Control group (no leukemia) (n = 500) | p-value |
|---|---|---|---|---|
| Age M ± SD | | 36.78 ± 11.50 | 38.41 ± 8.65 | 0.02 [b] |
| Habit of cigarette smoking | Yes | 115 (57.5) | 280 (56.0) | <0.01 [a] |
| | No | 85 (42.5) | 220 (44.0) | |
| Habit of alcohol drinking | Group of high alcohol consumption | 110 (55.0) | 290 (58.0) | 0.06 [a] |
| | Group of low alcohol consumption | 90 (45.0) | 210 (42.0) | |
| Family medical history | Yes | 130 (65.0) | 150 (30.0) | 0.88 [a] |
| | No | 70 (35.0) | 350 (70.0) | |

TABLE 15

| Item | | Case study group (leukemia) (n = 200) | Control group (no leukemia) (n = 200) | p-value |
|---|---|---|---|---|
| Gender | Male | 100 (50.0) | 100 (50.0) | 0.69 |
| | Female | 100 (50.0) | 100 (50.0) | |
| Age M ± SD | | 36.78 ± 11.50 | 40.68 ± 5.33 | 0.03 [b] |
| Habit of cigarette smoking | Yes | 115 (57.5) | 120 (60.0) | 0.02 [a] |
| | No | 85 (42.5) | 80 (40.0) | |
| Habit of alcohol drinking | Group of high alcohol consumption | 110 (55.0) | 130 (65.0) | 0.04 [a] |
| | Group of low alcohol consumption | 90 (45.0) | 70 (35.0) | |
| Family medical history | Yes | 130 (65.0) | 140 (70.0) | 0.23 [a] |
| | No | 70 (35.0) | 60 (30.0) | |

Table 14 is another statistical table of the third research data. Table 15 is another statistical table of the fourth research data. Referring to Table 14 and Table 15, in this embodiment, the processing unit 40 can perform analysis and calculation according to a test algorithm, to obtain statistical tests that respectively correspond to the second parameter and that are in the third research data and the fourth research data (that is, step S04). An annotation a in the p-value field is obtained according to the Chi-square test algorithm. An annotation b in the p-value field is obtained according to the T-test algorithm. A level of significance is 5%.

For example, Table 14 shows descriptive and inferential statistics. In descriptive statistics, distribution of data of continuous variables is presented by using an average value and a standard deviation, and distribution of data of categorical variables is presented by using a case number and a percentage. In inferential statistics, a difference between average values of ages of the case study group and the control group is explored by using a T-test, and whether there is relevance between whether there is leukemia and other attribute factors than an age can be explored by using a Chi-square test. Therefore, it may be found according to results displayed in Table 14 that, there is a statistically significant difference or significant relevance between distribution of ages and habits of cigarette smoking in leukemia and no leukemia (p<0.05). In addition, Table 15 also shows other descriptive and inferential statistics. It may be found according to results displayed in Table 15 that, there is a statistically significant difference or significant relevance between distribution of ages, habits of cigarette smoking, and habits of alcohol drinking in leukemia and no leukemia (p<0.05).

TABLE 16

| Item | | Coefficient estimated value | Odds ratio (OR) (95% CI) | p-value |
|---|---|---|---|---|
| Single-factor analysis | | | | |
| Gender | Male | 0.163 | 1.161 (1.515, 2.298) | 0.088 |
| | Female | | | |
| Age | | 0.438 | 1.587 (1.235, 1.981) | 0.018 |
| Habit of cigarette smoking | Yes | 0.831 | 2.605 (2.005, 2.898) | 0.049 |
| | No | | | |
| Habit of alcohol drinking | Group of high alcohol consumption | 0.101 | 1.003 (0.805, 1.155) | 0.063 |
| | Group of low alcohol consumption | | | |
| Family medical history | Yes | 0.285 | 1.264 (2.045, 2.365) | 0.174 |
| | No | | | |
| | Yes | 0.745 | 2.431 (1.911, 2.666) | 0.029 |
| | No | | | |
| Multiple-factor analysis | | | | |
| Gender | Male | 0.139 | 1.028 (0.789, 1.268) | 0.072 |
| | Female | | | |
| Age | | 0.288 | 1.267 (0.998, 1.556) | 0.031 |
| Habit of cigarette smoking | Yes | 0.741 | 2.123 (1.995, 2.394) | 0.061 |
| | No | | | |
| Habit of alcohol drinking | Group of high alcohol consumption | 0.022 | 1.011 (0.805, 1.172) | 0.105 |
| | Group of low alcohol consumption | | | |
| Family medical history | Yes | 0.402 | 1.574 (1.284, 1.961) | 0.201 |
| | No | | | |
| Exposure to styrene | Yes | 0.538 | 1.888 (0.998, 2.001) | 0.015 |
| | No | | | |

TABLE 17

| Item | | Coefficient estimated value | Odds ratio (OR) (95% CI) | p-value |
|---|---|---|---|---|
| Single-factor analysis | | | | |
| Gender | Male | 0.102 | 1.067 (0.879, 1.266) | 0.062 |
| | Female | | | |
| Age | | 0.201 | 1.336 (0.999, 1.642) | 0.045 |
| Habit of cigarette smoking | Yes | 0.225 | 1.338 (0.999, 1.956) | 0.068 |
| | No | | | |
| Habit of alcohol drinking | Group of high alcohol consumption | 0.138 | 1.113 (0.872, 1.336) | 0.108 |
| | Group of low alcohol consumption | | | |
| Family medical history | Yes | 0.421 | 1.682 (1.251, 1.999) | 0.048 |
| | No | | | |
| Exposure to styrene | Yes | 0.520 | 1.826 (1.529, 2.061) | 0.031 |
| | No | | | |
| Multiple-factor analysis | | | | |
| Gender | Male | 0.142 | 1.043 (0.861, 1.333) | 0.072 |
| | Female | | | |
| Age | | 0.299 | 1.527 (1.329, 1.866) | 0.054 |
| Habit of cigarette smoking | Yes | 0.201 | 1.307 (1.225, 1.842) | 0.105 |
| | No | | | |
| Habit of alcohol drinking | Group of high alcohol consumption | 0.109 | 1.027 (1.005, 1.365) | 0.087 |
| | Group of low alcohol consumption | | | |
| Family medical history | Yes | 0.555 | 1.851 (1.784, 1.997) | 0.087 |
| | No | | | |
| Exposure to styrene | Yes | 0.493 | 1.812 (1.655, 2.103) | 0.018 |
| | No | | | |

Table 16 is a statistical table of logistic regression results of the third research data. Table 17 is a statistical table of conditional logistic regression results of the fourth research data. In an embodiment, the processing unit 40 can also obtain a corresponding result according to the statistical hypothesis testing algorithm, the single-factor/multiple-factor analysis algorithm, or another test algorithm. For example, in the third research data, referring to Table 16, results of relevance between a single factor and multiple factors and leukemia are explored by using a logistic regression analysis method. Results obtained from the single-factor analysis show that, an age, a habit of cigarette smoking and exposure to styrene are both statistically related to developing leukemia (p<0.05). Results obtained from the multiple-factor analysis show that, there is statistical relevance between an age and exposure to styrene and developing leukemia (p<0.05). As an age increases annually, odds of developing leukemia are increased by 26.7%, and odds of developing leukemia by a person who is exposed to styrene are 1.888 times that of developing leukemia by a person who is not exposed to styrene. That is, odds of developing leukemia by a person who is exposed to styrene are increased by 88.8%, and an upper limit of a confidence interval of the odds ratio shows that the odds may be increased up to 100.1%. Similarly, in the fourth research data, referring to Table 17, results of relevance between a single factor and multiple factors and leukemia are explored by using a conditional logistic regression analysis method. Results obtained from the single-factor analysis show that, an age, a family medical history, and exposure to styrene are all statistically related to developing leukemia (p<0.05). Results obtained from the multiple-factor analysis show that, there is statistical relevance between only exposure to styrene and developing leukemia (p<0.05), and odds of developing leukemia by a person who is exposed to styrene are 1.812 times that of developing leukemia by a person who is not exposed to styrene. That is, odds of developing leukemia by a person who is exposed to styrene are increased by 81.2%, and an upper limit of a confidence interval of the odds ratio shows that the odds may be increased up to 110.3%.

Finally, the processing unit 40 integrates the foregoing first parameter, second parameter, statistical information, and statistical tests into integration information (similar to Table 7 in the first embodiment, and a display result thereof may be determined according to an actual requirement) by using the integration algorithm according to the foregoing various results obtained through analysis and calculation, and transmits the integration information to the display unit 50 for display.

In a fourth embodiment, the researcher is intended to research relevance between whether it is in a high temperature region (the first parameter) and whether an ice crusher is bought (the second parameter). First, members in January 2010 to December 2014 as research and observation objects are stored in the database 60. The number of members who have bought an ice crusher beyond a research period is subtracted, and an actual number of research objects is 5,000. Therefore, the researcher can operate the control unit 30 to select the first research approach, and select the first parameter as whether a person lives in a high temperature region, and select the second parameter as whether a person buys an ice crusher (step S01).

TABLE 18

|  | Event occurring (buying an ice crusher) | Event not occurring (buying no ice crusher) | Total |
|---|---|---|---|
| Exposure to a high temperature region (mean daily temperature ≥ 28° C.) | 200 | 800 | 1,000 |
| No exposure to a high temperature region (mean daily temperature < 28° C.) | 600 | 3,400 | 4,000 |
| Total | 800 | 4,200 | 5,000 |

Table 18 is a statistical table of the first research approach in the fourth embodiment. Herein, the processing unit 40 can find and receive, from database 60, various pieces of research data corresponding to the first research approach, the first parameter, and the second parameter (as shown in Table 18) (step S02). Next, the processing unit 40 can perform calculation according to a statistical algorithm, to generate statistical information (step S03). For example, the processing unit 40 can calculate an occurrence rate for each piece of research data according to the occurrence rate algorithm. For example, an occurrence rate of buying an ice crusher in a high temperature region=(200/1,000)× 1000‰=200‰, that is, among every thousand persons who are exposed to a high temperature region (a mean daily temperature≥28° C.), there are 200 persons who buy an ice crusher. An occurrence rate of buying an ice crusher by persons who are not exposed to a high temperature region= (600/4,000)×1000‰=150‰, that is, among every thousand persons who are not exposed to a high temperature region (a mean daily temperature<28° C.), there are 150 persons who buy an ice crusher. An occurrence rate of buying an ice crusher for the entire population=(800/5,000)× 1000‰=160‰, that is, among every thousand persons, there are 160 persons who buy an ice crusher.

In some embodiments, the processing unit 40 can also perform calculation according to the relative risk algorithm, the odds ratio algorithm, or another statistical algorithm, to generate statistical information. For example, in the relative risk algorithm, an occurrence rate of buying an ice crusher by persons living in a high temperature region/an occurrence rate of buying an ice crusher by persons not living in a high temperature region=200‰/150‰=1.33, indicating that a possibility of buying an ice crusher by a person who is exposed to a high temperature region is 1.33 times that of buying an ice crusher by a person who is not exposed to a high temperature region; that is, a possibility of buying an ice crusher by a person who is exposed is 1.33 times that of buying an ice crusher by a person who is not exposed. In addition, the processing unit 40 can obtain through calculation by using the odds ratio algorithm that an odds ratio= (200/800)/(600/3,400)=1.42, indicating that odds of buying an ice crusher by a person who is exposed to a high temperature region are 1.42 times of that of buying an ice crusher by a person who is not exposed to a high temperature region.

TABLE 19

|  | Case number (%) | | |
|---|---|---|---|
| Item | Exposure to a high temperature region (mean daily temperature ≥ 28° C.) (n = 800) | No exposure to a high temperature region (mean daily temperature < 28° C.) (n = 4,200) | p-value |
| Gender |  |  | <0.01 |
| Male | 350 (43.7) | 2,000 (47.6) |  |
| Female | 450 (56.3) | 2,200 (52.4) |  |
| Age |  |  |  |
| Up to the age of 29 | 300 (37.5) | 1,400 (33.4) | 0.041 |
| The age from 30 to 49 | 400 (50.0) | 2,000 (47.6) |  |
| The age of 50 and more | 100 (12.5) | 800 (19.0) |  |
| Living region |  |  |  |
| Northern region | 450 (56.3) | 2,000 (47.6) | 0.039 |
| Central region | 200 (25.0) | 1,200 (28.6) |  |
| Southern region | 150 (18.7) | 1,000 (23.8) |  |

Table 19 is a descriptive and inferential statistical table corresponding to the first research approach in the fourth embodiment. The p-value is learned of according to the Chi-square test algorithm. In descriptive statistics, distribution of data of categorical variables is presented by using a case number and a percentage. In inferential statistics, whether there is relevance between whether it is exposed to high temperature region and an attribute factor is explored by using a Chi-square test.

Next, the processing unit 40 can perform analysis and calculation according to a test algorithm, to generate a statistical test (step S04). For example, referring to Table 19, the processing unit 40 can obtain each p-value by using the Chi-square test algorithm. It may be that there is statistically significant relevance between a gender, an age, a living region, and whether it is exposed to a high temperature region ($p<0.05$), that is, there is a statistically significant difference between distribution of exposure and no exposure to a high temperature region in ages, genders, and living regions.

TABLE 20

| Item | | Coefficient estimated value | Indicator of estimated value Hazard ratio (HR) (95% CI) | p-value |
|---|---|---|---|---|
| Single-factor analysis | | | | |
| Gender | Male | 0.137 | 1.206 (1.118, 1.369) | 0.053 |
| | Female | | | |
| Age | The age of 50 and more | 0.094 | 1.154 (1.008, 1.326) | 0.057 |
| | The age from 30 to 49 | 0.169 | 1.896 (0.986, 2.201) | 0.061 |
| | Up to the age of 29 | | | |
| Living region | Southern region | 0.441 | 2.666 (1.758, 3.097) | 0.018 |
| | Central region | 0.320 | 2.379 (1.666, 2.691) | 0.029 |
| | Northern region | | | |
| Mean daily temperature in the living region | ≥28° C. | 0.287 | 2.305 (1.556, 2.852) | 0.030 |
| | <28° C. | | | |
| Multiple-factor analysis | | | | |
| Gender | Male | 0.043 | 1.051 (1.025, 1.322) | 0.068 |
| | Female | | | |
| Age | The age of 50 and more | 0.148 | 1.145 (1.036, 1.514) | 0.112 |
| | The age from 30 to 49 | 0.162 | 1.312 (0.986, 1.842) | 0.101 |
| | Up to the age of 29 | | | |
| Living region | Southern region | 0.358 | 2.521 (1.742, 4.215) | 0.065 |
| | Central region | 0.304 | 2.011 (1.422, 3.923) | 0.057 |
| | Northern region | | | |
| Mean daily temperature in the living region | ≥28° C. | 0.309 | 2.013 (1.413, 3.928) | 0.034 |
| | <28° C. | | | |

Table 20 is a statistical table of Cox regression analysis results in the fourth embodiment. Referring to Table 20, results obtained from the single-factor analysis show that, a living region and a mean daily temperature in the living region are both statistically related to buying an ice crusher ($p<0.05$). Results obtained from the multiple-factor analysis show that, only a mean daily temperature in a living region is a significant influencing factor for buying an ice crusher, and there is statistical relevance between the two ($p<0.05$). As the mean daily temperature in the living region increases by 1° C. each time, odds (a possibility) of buying an ice crusher are increased by 101.3%.

TABLE 21

| Item | Coefficient estimated value (95% CI) | p-value |
|---|---|---|
| Up to the age of 29 | −5.863 (−7.613, −6.927) | 0.056 |
| The age from 30 to 49 | 1.501 (1.051, 1.961) | 0.052 |
| The age of 50 and more | 1.324 (0.825, 1.716) | 0.057 |

Table 21 is a statistical table of Poisson regression results of an occurrence rate of buying an ice crusher and age in the fourth embodiment. Referring to Table 21, the processing unit 40 further divides ages into three age groups: up to the age of 29, the age from 30 to 49, and the age of 50 and more. An occurrence rate of buying an ice crusher for a basal age group (up to the age of 29) is estimated to be $e^{\beta_0}=e^{-5.863}=0.003$. Occurrence rates of buying an ice crusher for age groups of the age from 30 to 49 and the age of 50 and more are respectively estimated to be $e^{-5.863+1.501}=0.013$ and $e^{-5.863+1.324}=0.011$. Occurrence rate ratio values (IRR) of buying an ice crusher for the age groups compared with the basal age group (up to the age of 29) are respectively 4.486 and 3.758. Therefore, it may be learned from the p-values in Table 21 that, an age group is not significantly related to an occurrence rate of buying an ice crusher.

TABLE 22

| Item | | Coefficient estimated value | Odds ratio (OR) (95% CI) | p-value |
|---|---|---|---|---|
| Single-factor analysis | | | | |
| Gender | Male | 0.361 | 2.022 (1.876, 2.666) | 0.083 |
| | Female | | | |
| Age | The age of 50 and more | 0.155 | 1.153 (0.998, 1.331) | 0.062 |
| | The age from 30 to 49 | 0.201 | 1.684 (0.882, 1.871) | 0.071 |
| | Up to the age of 29 | | | |
| Living region | Southern region | 0.498 | 2.306 (1.981, 3.229) | 0.051 |
| | Central region | 0.307 | 2.006 (1.674, 2.236) | 0.053 |
| | Northern region | | | |
| Mean daily temperature in the living region | ≥28° C. | 0.520 | 2.339 (1.887, 2.528) | 0.014 |
| | <28° C. | | | |
| Multiple-factor analysis | | | | |
| Gender | Male | 0.341 | 2.126 (1.442, 3.913) | 0.074 |
| | Female | | | |
| Age | The age of 50 and more | 0.149 | 1.426 (0.261, 1.652) | 0.063 |
| | The age from 30 to 49 | 0.158 | 1.503 (0.416, 1.852) | 0.069 |
| | Up to the age of 29 | | | |
| Living region | Southern region | 0.368 | 2.231 (1.742, 4.214) | 0.072 |
| | Central region | 0.318 | 2.043 (0.516, 2.546) | 0.064 |
| | Northern region | | | |
| Mean daily temperature in the living region | ≥28° C. | 0.321 | 2.052 (0.617, 2.825) | 0.026 |
| | <28° C. | | | |

Table 22 is a statistical table of logistic regression results of factors related to buying an ice crusher in the fourth embodiment. Therefore, it may be learned from Table 22 that, results obtained from the single-factor analysis show that, a mean daily temperature in a living region is statistically related to buying an ice crusher ($p<0.05$). Results obtained from the multiple-factor analysis show that, a mean daily temperature in a living region is a significant influencing factor for buying an ice crusher, and there is statistical relevance between the two ($p<0.05$). As the mean daily temperature in the living region increases by 1° C. each time, odds of buying an ice crusher are increased by 105.2%.

Next, the processing unit 40 integrates the foregoing first parameter, second parameter, various pieces of statistical information, and statistical tests into integration information according to the integration algorithm (step S05), and transmits the integration information to the display unit 50, so that the display unit 50 displays the integration information. The researcher can rapidly understand relevance between the first parameter and the second parameter, and further, the general population can understand the meaning of a research result thereof.

Table 23 is a statistical table related to fifth research data in the second research approach in a fifth embodiment. Table 24 is a statistical table related to sixth research data in the second research approach in the fifth embodiment. In the fifth embodiment, the same as the second embodiment, the researcher can operate the control unit 30 to select the second research approach, and select the first parameter as whether a person lives in a high temperature region, and select the second parameter as whether a person buys an ice crusher (step S01). In the fifth research data, 800 members who buy an ice crusher from an online store in January 2010 to December 2014 are selected as a case study group. 2,000 members who buy no ice crusher from an online store within the same period are selected as a control group. In the sixth research data, 800 members who buy an ice crusher from an online store in January 2010 to December 2014 are selected as a case study group. By means of 1:1 paring, 800 members having same genders as cases and having a no more than 2-year age gap from the cases are selected as a control group, and there are 800 pairs in total (step S02).

TABLE 23

|  | Case study group (buying an ice crusher) | Control group (buying no ice crusher) | Total |
|---|---|---|---|
| Exposure to a high temperature region (mean daily temperature ≥ 28° C.) | 440 | 1,000 | 1,440 |
| No exposure to a high temperature region (mean daily temperature < 28° C.) | 360 | 1,000 | 1,360 |
| Total | 800 | 2,000 | 2,800 |

TABLE 24

|  | Control group (buying an ice crusher) | | |
|---|---|---|---|
| Case study group (buying an ice crusher) | Exposure to a high temperature region (mean daily temperature ≥ 28° C.) | No exposure to a high temperature region (mean daily temperature < 28° C.) | Total |
| Exposure to a high temperature region (mean daily temperature ≥ 28° C.) | 180 | 270 | 450 |
| No exposure to a high temperature region (mean daily temperature < 28° C.) | 150 | 200 | 350 |
| Total | 330 | 470 | 800 |

Next, the processing unit 40 can calculate an exposure rate (statistical information) for the fifth research data and an exposure rate (statistical information) for the sixth research data according to an exposure algorithm (a statistical algorithm) (step S03). For example, an exposure rate of the case study group in the fifth research data=(440/800)×100%=55%, that is, among the 800 members who buy an ice crusher, there are 440 persons who are exposed to a high temperature region, and the exposure rate is 55%. An exposure rate of the control group thereof=(1,000/2,000)×100%=50%, that is, among the 2,000 members who buy no ice crusher, there are 1,000 persons who are exposed to a high temperature region, and the exposure rate is 50%. For example, an exposure rate of the case study group in the sixth research data=(450/800)×100%=56.25%, that is, among the 800 members who buy an ice crusher, there are 450 persons who are exposed to a high temperature region, and the exposure rate is 56.25%. An exposure rate of the control group thereof=(330/800)×100%=41.25%, that is, among the 800 members who buy no ice crusher, there are 330 persons who are exposed to a high temperature region, and the exposure rate is 41.25%.

In addition, the processing unit 40 can also separately perform calculation by using a statistical algorithm of another type, to obtain statistical information thereof (step S03). For example, an odds ratio in the fifth research data=(440*1000)/(1000*360)=1.2, indicating that exposure odds for buying an ice crusher are 1.2 times that for buying no ice crusher, that is, odds of being exposed to a high temperature region by a person who buys an ice crusher are 1.2 times that of being exposed to a high temperature region by a person who buys no ice crusher. An odds ratio in the sixth research data=270/150=1.8, indicating that exposure odds for buying an ice crusher are 1.8 times that for buying no ice crusher, that is, odds of being exposed to a high temperature region by a person who buys an ice crusher are 1.8 times that of being exposed to a high temperature region by a person who buys no ice crusher. A calculation manner for other statistical information is not described in detail herein.

Table 25 is a descriptive and inferential statistical table corresponding to the second research approach in the fifth embodiment. Table 26 is another descriptive and inferential statistical table corresponding to the second research approach in the fifth embodiment. Next, the processing unit 40 separately analyzes the fifth research data, the sixth research data, and the second parameter according to a test algorithm, to learn of statistical tests (step S04). For example, in table 25, in descriptive statistics, distribution of data of categorical variables is presented by using a case number and a percentage. In inferential statistics, whether there is relevance between whether an ice crusher is bought and an attribute factor is explored by using a Chi-square test. It may be found from results displayed in Table 25 that, there is a statistically significant difference or significant relevance between distribution of ages and living regions in buying an ice crusher and buying no ice crusher (p<0.05). In table 26, in descriptive statistics, distribution of data of categorical variables is presented by using a case number and a percentage. In inferential statistics, whether there is relevance between whether an ice crusher is bought and an attribute factor is explored by using a Chi-square test. It may be found from results displayed in Table 26 that, there is a statistically significant difference or significant relevance between distribution of ages and living regions in buying an ice crusher and buying no ice crusher (p<0.05).

TABLE 25

| | | Case number (%) | | |
| --- | --- | --- | --- | --- |
| | Item | Case study group (buying an ice crusher) (n = 800) | Control group (buying no ice crusher) (n = 2,000) | p-value |
| Gender | Male | 450 (56.3) | 1,150 (57.5) | 0.22 |
| | Female | 350 (43.7) | 850 (42.5) | |
| Age | Up to the age of 29 | 300 (37.5) | 1000 (50.0) | 0.03 |
| | The age from 30 to 49 | 350 (43.8) | 400 (20.0) | |
| | The age of 50 and more | 150 (18.7) | 600 (30.0) | |
| Living region | Northern region | 290 (36.3) | 400 (20.0) | 0.01 |
| | Central region | 260 (32.5) | 650 (32.5) | |
| | Southern region | 250 (31.2) | 950 (47.5) | |

TABLE 26

| | | Case number (%) | | |
| --- | --- | --- | --- | --- |
| | Item | Case study group (buying an ice crusher) (n = 800) | Control group (buying no ice crusher) (n = 800) | p-value |
| Gender | Male | 450 (56.3) | 450 (56.3) | 0.12 |
| | Female | 350 (43.7) | 350 (43.7) | |
| Age | Up to the age of 29 | 300 (37.5) | 400 (50.0) | 0.03 |
| | The age from 30 to 49 | 350 (43.8) | 200 (25.0) | |
| | The age of 50 and more | 150 (18.7) | 200 (25.0) | |
| Living region | Northern region | 290 (36.3) | 350 (43.8) | 0.02 |
| | Central region | 260 (32.5) | 300 (37.5) | |
| | Southern region | 250 (31.2) | 150 (18.7) | |

Table 27 is a statistical table of logistic regression analysis on the fifth research data in the fifth embodiment. Table 28 is a statistical table of conditional logistic regression analysis on the sixth research data in the fifth embodiment. It may be learned from Table 27 that, results obtained from the single-factor analysis show that, a living region and a mean daily temperature in the living region are both statistically related to buying an ice crusher (p<0.05). Results obtained from the multiple-factor analysis show that, there is statistical relevance between only a mean daily temperature in a living region and buying an ice crusher (p<0.05). As the mean daily temperature in the living region increases by 1° C. each time, odds of buying an ice crusher are increased by 222.3%. It may be learned from Table 27 that, results obtained from the single-factor analysis show that, a living region and a mean daily temperature in the living region are both statistically related to buying an ice crusher (p<0.05). Results obtained from the multiple-factor analysis show that, there is statistical relevance between only a mean daily temperature in a living region and buying an ice crusher (p<0.05). As the mean daily temperature in the living region increases by 1° C. each time, odds of buying an ice crusher are increased by 198.6%.

TABLE 27

| Item | | Coefficient estimated value | Odds ratio (OR) (95% CI) | p-value |
| --- | --- | --- | --- | --- |
| Single-factor analysis | | | | |
| Gender | Male | 0.651 | 2.155 (1.515, 2.298) | 0.068 |
| | Female | | | |
| Age | The age of 50 and more | 0.079 | 1.053 (0.904, 1.221) | 0.251 |
| | The age from 30 to 49 | 0.184 | 1.169 (0.896, 1.339) | 0.188 |
| | Up to the age of 29 | | | |
| Living region | Southern region | 0.555 | 1.431 (1.258, 1.666) | 0.045 |
| | Central region | 0.317 | 1.222 (0.956, 1.356) | 0.048 |
| | Northern region | | | |
| Mean daily temperature in the living region | ≥28° C. <28° C. | 0.732 | 2.638 (1.998, 3.006) | 0.022 |
| Multiple-factor analysis | | | | |
| Gender | Male | 0.368 | 1.659 (1.520, 2.079) | 0.109 |
| | Female | | | |
| Age | The age of 50 and more | 0.034 | 1.013 (0.956, 1.377) | 0.184 |
| | The age from 30 to 49 | 0.591 | 2.061 (1.998, 2.369) | 0.116 |
| | Up to the age of 29 | | | |
| Living region | Southern region | 0.779 | 2.612 (1.723, 2.888) | 0.081 |
| | Central region | 0.204 | 1.554 (1.125, 1.978) | 0.063 |
| | Northern region | | | |
| Mean daily temperature in the living region | ≥28° C. <28° C. | 1.067 | 3.223 (2.055, 3.365) | 0.002 |

TABLE 28

| Item | | Coefficient estimated value | Odds ratio (OR) (95% CI) | p-value |
| --- | --- | --- | --- | --- |
| Single-factor analysis | | | | |
| Gender | Male | 0.537 | 1.428 (0.997, 1.666) | 0.112 |
| | Female | | | |
| Age | The age of 50 and more | 0.081 | 1.034 (0.998, 1.356) | 0.187 |
| | The age from 30 to 49 | 0.397 | 1.255 (0.793, 1.384) | 0.093 |
| | Up to the age of 29 | | | |
| Living region | Southern region | 0.710 | 1.692 (1.528, 1.872) | 0.044 |
| | Central region | 0.521 | 1.417 (0.871, 1.998) | 0.041 |
| | Northern region | | | |

TABLE 28-continued

| Item | | Coefficient estimated value | Odds ratio (OR) (95% CI) | p-value |
|---|---|---|---|---|
| Mean daily temperature in the living region | ≥28° C. <28° C. | 0.829 | 2.064 (2.999, 3.344) | 0.011 |
| Multiple-factor analysis | | | | |
| Gender | Male Female | 0.840 | 1.687 (1.423, 1.998) | 0.057 |
| Age | The age of 50 and more | 0.097 | 1.009 (0.661, 1.339) | 0.283 |
| | The age from 30 to 49 | 0.429 | 1.211 (0.956, 1.347) | 0.179 |
| | Up to the age of 29 | | | |
| Living region | Southern region | 0.842 | 1.688 (0.997, 1.843) | 0.112 |
| | Central region | 0.806 | 1.641 (1.008, 2.076) | 0.134 |
| | Northern region | | | |
| Mean daily temperature in the living region | ≥28° C. <28° C. | 1.387 | 2.986 (2.671, 3.118) | 0.004 |

Next, the processing unit 40 can integrate the foregoing obtained fifth research data, sixth research data, first parameter, second parameter, statistical information, and statistical tests by using the integration algorithm, to generate integration information (step S05), so that the display unit 50 displays the integration information.

Table 29 is a statistical table related to seventh research data in the third research approach in a sixth embodiment. Table 30 is a statistical table related to eighth research data in the third research approach in the sixth embodiment. In the sixth embodiment, the same as the third embodiment, the researcher can operate the control unit 30 to select the third research approach, and select the first parameter as whether a person lives in a high temperature region, and select the second parameter as whether a person buys an ice crusher (step S01). Members (the number of members who have bought an ice crusher beyond a research period is subtracted) of an online store in January 2010 to December 2014 as research objects are stored in the database 60. Therefore, in the seventh research data, 800 members who buy an ice crusher from an online store in January 2010 to December 2014 are selected as a case study group. 2,000 members who buy no ice crusher from an online store within the same period are selected as a control group. In the eighth research data, 800 members who buy an ice crusher from an online store in January 2010 to December 2014 are selected as a case study group. By means of 1:1 paring, 800 members having same genders as cases and having a no more than 2-year age gap from the cases are selected as a control group, and there are 800 pairs in total (for example, step S02).

TABLE 29

| | Case study group (buying an ice crusher) | Control group (buying no ice crusher) | Total |
|---|---|---|---|
| Exposure to a high temperature region (mean daily temperature ≥ 28° C.) | 480 | 900 | 1,380 |

TABLE 29-continued

| | Case study group (buying an ice crusher) | Control group (buying no ice crusher) | Total |
|---|---|---|---|
| No exposure to a high temperature region (mean daily temperature < 28° C.) | 320 | 1,100 | 1,420 |
| Total | 800 | 2,000 | 2,800 |

TABLE 30

| | Control group (buying no ice crusher) | | |
|---|---|---|---|
| | Exposure to a high temperature region (mean daily temperature ≥ 28° C.) | No exposure to a high temperature region (mean daily temperature < 28° C.) | Total |
| Case study group (buying an ice crusher) | | | |
| Exposure to a high temperature region (mean daily temperature ≥ 28° C.) | 150 | 300 | 450 |
| No exposure to a high temperature region (mean daily temperature < 28° C.) | 100 | 250 | 350 |
| Total | 250 | 550 | 800 |

Next, the processing unit 40 can perform calculation by using a statistical algorithm, to obtain statistical information of the seventh research data and the eighth research data (for example, step S03). For example, the processing unit 40 can calculate, according to the occurrence rate algorithm, an occurrence rate of buying an ice crusher for the seventh research data, and the occurrence rate thereof=(800/2,800)×1000‰=285.7‰, that is, among every thousand persons, there are 285.7 persons who buy an ice crusher. Similarly, an occurrence rate of buying an ice crusher for the eighth research data=(800/1,600)×1000‰=500‰, that is, among every thousand persons, there are 500 persons who buy ice crusher.

In some embodiments, the processing unit 40 can also perform calculation for the seventh research data and the eighth research data according to the odds ratio algorithm, to obtain statistical information of odds ratios. For example, when the processing unit 40 performs calculation for the seventh research data according to the odds ratio algorithm, the odds ratio thereof=(480*1,100)/(900*320)=1.83, indicating that exposure odds for buying an ice crusher are 1.83 times that for buying no ice crusher, that is, odds of being exposed to a high temperature region by a person who buys an ice crusher are 1.83 times that of being exposed to a high temperature region by a person who buys no ice crusher. Similarly, the odds ratio in the eighth research data=300/100=3, indicating that exposure odds for buying an ice crusher are 3 times that for buying no ice crusher, that is, odds of being exposed to a high temperature region by a person who buys an ice crusher are 3 times that of being exposed to a high temperature region by a person who buys no ice crusher. In some embodiments, the processing unit 40 can further perform calculation for the seventh research data or the eighth research data according to a statistical algorithm of another type, to generate corresponding statistical information. The present invention is not limited thereto.

Table 31 is a statistical test table of the seventh research data in the sixth embodiment. Table 32 is a statistical test table of the eighth research data in the sixth embodiment. The processing unit 40 can perform calculation for the seventh research data and the eighth research data by using a test algorithm, to generate statistical tests (for example, step S04). For example, Table 31 is a statistical table obtained after calculation is performed for the seventh research data by using the Chi-square test algorithm, and includes descriptive and inferential statistics. In descriptive statistics, distribution of data of categorical variables is presented by using a case number and a percentage. In inferential statistics, whether there is relevance between whether an ice crusher is bought and an attribute factor is explored by using a Chi-square test. It may be found from results that, there is a statistically significant difference or significant relevance between distribution of ages and living regions in buying an ice crusher and buying no ice crusher (p<0.05). Similarly, Table 32 is a statistical table obtained after calculation is performed for the eighth research data by using the Chi-square test algorithm, and includes descriptive and inferential statistics. In descriptive statistics, distribution of data of categorical variables is presented by using a case number and a percentage. In inferential statistics, whether there is relevance between whether an ice crusher is bought and an attribute factor is explored by using a Chi-square test. It may be found from results that, there is a statistically significant difference or significant relevance between distribution of ages and living regions in buying an ice crusher and buying no ice crusher (p<0.05).

TABLE 31

| | Item | Case study group (buying an ice crusher) (n = 800) | Control group (buying no ice crusher) (n = 2,000) | p-value |
|---|---|---|---|---|
| Gender | Male | 480 (60.0) | 800 (40.0) | 0.07 |
| | Female | 320 (40.0) | 1,200 (60.0) | |
| Age | Up to the age of 29 | 320 (40.0) | 840 (42.0) | 0.02 |
| | The age from 30 to 49 | 260 (32.5) | 590 (29.5) | |
| | The age of 50 and more | 220 (27.5) | 570 (28.5) | |
| Living region | Northern region | 290 (36.3) | 750 (37.5) | 0.03 |
| | Central region | 370 (46.2) | 420 (21.0) | |
| | Southern region | 140 (17.5) | 830 (41.5) | |

TABLE 32

| | Item | Case study group (buying an ice crusher) (n = 800) | Control group (buying no ice crusher) (n = 800) | p-value |
|---|---|---|---|---|
| Gender | Male | 480 (60.0) | 480 (60.0) | 0.10 |
| | Female | 320 (40.0) | 320 (40.0) | |
| Age | Up to the age of 29 | 320 (40.0) | 210 (26.3) | 0.03 |
| | The age from 30 to 49 | 260 (32.5) | 340 (42.5) | |
| | The age of 50 and more | 220 (27.5) | 250 (31.2) | |
| Living region | Northern region | 290 (36.3) | 200 (25.0) | 0.01 |
| | Central region | 370 (46.2) | 240 (30.0) | |
| | Southern region | 140 (17.5) | 360 (45.0) | |

In addition, in some embodiments, the processing unit 40 can perform analysis and calculation for the seventh research data according to a logistic regression analysis algorithm (a test algorithm), and the processing unit 40 can perform analysis for the eighth research data according to a conditional logistic regression analysis algorithm (a test algorithm), to further obtain corresponding statistical tests. Table 33 is another statistical test table of the seventh research data in the sixth embodiment, Table 34 is another statistical test table of the eighth research data in the sixth embodiment.

TABLE 33

| | Item | Coefficient estimated value | Odds ratio (OR) (95% CI) | p-value |
|---|---|---|---|---|
| Single-factor analysis | | | | |
| Gender | Male | 0.267 | 1.159 (1.001, 1.673) | 0.068 |
| | Female | | | |
| Age | The age of 50 and more | 0.073 | 1.091 (0.998, 1.246) | 0.137 |
| | The age from 30 to 49 | 0.481 | 1.338 (1.097, 1.614) | 0.126 |
| | Up to the age of 29 | | | |
| Living region | Southern region | 0.622 | 1.597 (0.997, 1.999) | 0.066 |
| | Central region | 0.789 | 1.669 (1.367, 2.119) | 0.092 |
| | Northern region | | | |
| Mean daily temperature in the living region | ≥28° C. | 1.007 | 2.227 (1.892, 2.377) | 0.032 |
| | <28° C. | | | |
| Multiple-factor analysis | | | | |
| Gender | Male | 0.272 | 1.116 (0.746, 1.658) | 0.067 |
| | Female | | | |
| Age | The age of 50 and more | 0.153 | 1.073 (0.888, 1.231) | 0.091 |
| | The age from 30 to 49 | 0.303 | 1.207 (0.944, 1.761) | 0.086 |
| | Up to the age of 29 | | | |
| Living region | Southern region | 0.978 | 2.341 (1.902, 2.009) | 0.062 |
| | Central region | 0.661 | 1.763 (1.429, 2.007) | 0.057 |
| | Northern region | | | |

TABLE 33-continued

| Item | | Coefficient estimated value | Odds ratio (OR) (95% CI) | p-value |
|---|---|---|---|---|
| Mean daily temperature in the living region | ≥28° C. <28° C. | 1.457 | 3.764 (3.061, 3.999) | 0.003 |

TABLE 34

| Item | | Coefficient estimated value | Odds ratio (OR) (95% CI) | p-value |
|---|---|---|---|---|
| Single-factor analysis | | | | |
| Gender | Male | 0.222 | 1.166 (1.007, 1.669) | 0.044 |
| | Female | | | |
| Age | The age of 50 and more | 0.057 | 1.067 (0.557, 1.094) | 0.083 |
| | The age from 30 to 49 | 0.395 | 1.439 (1.339, 1.971) | 0.061 |
| | Up to the age of 29 | | | |
| Living region | Southern region | 1.009 | 2.302 (1.982, 2.790) | 0.047 |
| | Central region | 0.843 | 1.786 (0.999, 1.997) | 0.034 |
| | Northern region | | | |
| Mean daily temperature in the living region | ≥28° C. <28° C. | 1.531 | 2.773 (2.179, 2.999) | 0.007 |
| Multiple-factor analysis | | | | |
| Gender | Male | 0.189 | 1.173 (1.003, 2.003) | 0.064 |
| | Female | | | |
| Age | The age of 50 and more | 0.061 | 1.023 (0.661, 1.447) | 0.237 |
| | The age from 30 to 49 | 0.227 | 1.339 (1.223, 1.666) | 0.153 |
| | Up to the age of 29 | | | |
| Living region | Southern region | 0.999 | 2.057 (1.963, 2.580) | 0.099 |
| | Central region | 0.843 | 1.963 (1.627, 2.473) | 0.148 |
| | Northern region | | | |
| Mean daily temperature in the living region | ≥28° C. <28° C. | 1.780 | 2.996 (2.072, 3.297) | 0.012 |

Referring to Table 33 and Table 34, Table 33 and Table 34 are tables of statistical results of factors related to buying an ice crusher that are obtained by performing analysis by the processing unit 40 according to the logistic regression analysis algorithm. Results obtained from the single-factor analysis in Table 33 show that, a mean daily temperature in a living region is also statistically related to buying an ice crusher (p<0.05). Results obtained from the multiple-factor analysis show that, there is also statistical relevance between a mean daily temperature in a living region and buying an ice crusher (p<0.05). As the mean daily temperature in the living region increases by 1° C. each time, odds of buying an ice crusher are increased by 276.4%. In addition, the processing unit 40 performs analysis according to the conditional logistic regression analysis algorithm, to obtain a table of statistical results of factors related to buying an ice crusher. It may be learned from Table 34 that, results obtained from the single-factor analysis show that, a gender, a living region, and a mean daily temperature in the living region are all statistically related to buying an ice crusher (p<0.05). Results obtained from the multiple-factor analysis show that, there is statistical relevance between only a mean daily temperature in a living region and buying an ice crusher (p<0.05). As the mean daily temperature in the living region increases by 1° C. each time, odds of buying an ice crusher are increased by 199.6%. A test algorithm of another type is not described in detail herein.

Next, the processing unit 40 can integrate the foregoing first parameter, second parameter, various pieces of research data, various pieces of statistical information, and various statistical tests into integration information according to the integration algorithm (for example, step S05), and then transmit the integration information to the display unit 50, for display by the display unit 50 (for example, step S06). A technical feature of the integration information obtained by integration by using the integration algorithm is similar to that in the foregoing embodiments. A technical feature of the integration information displayed by the display unit 50 is similar to that in the foregoing embodiments, and details are not described herein again.

Selection of the first parameter and the second parameter is not limited in the present invention. In addition to the foregoing embodiments, the first parameter may be selected as whether a person is occupationally exposed to styrene, and the second parameter is whether a person buys an ice crusher; or the first parameter is whether it is in a high temperature region, and the second parameter is whether a person develops leukemia. That is, in the present invention, the first parameter and the second parameter can be randomly selected according to a user requirement.

According to the foregoing embodiments, the processing unit 40 can select, according to the researcher (or the user), a research approach and a to-be-researched event (that is, the first parameter and the second parameter), so as to rapidly integrate multiple research conclusions into integration information by using the integration algorithm. The researcher (or the user) can rapidly and intuitively understand, by using the display unit 50, relevance between the corresponding first parameter and second parameter in the research data, and can further study whether actually there is no relevance between a first parameter and a second parameter that are traditionally considered to have no relevance. Therefore, rapid research and analysis can be performed, to improve research efficiency, and applications and plans can be rapidly derived. In addition, according to the present invention, a result of a research issue that can be rapidly understood by a user in a non-professional field can be further provided, and a person in a non-professional field can understand a research result in a professional field.

What is claimed is:
1. A data analysis system, comprising:
   a transmission unit, configured to receive at least one piece of research data;
   a storage unit, configured to store various pieces of research data;
   a control unit, configured to generate a research approach, a first parameter, and a second parameter according to an operation instruction of a user, wherein the first parameter is a to-be-analyzed cause item, and the second parameter is a to-be-analyzed result item;

a processing unit, connected to the transmission unit, the storage unit, and the control unit, wherein the processing unit obtains the various pieces of research data by using the transmission unit according to the research approach, the first parameter, and the second parameter; the processing unit analyzes the first parameter, the second parameter, and the various pieces of research data by using a statistical algorithm according to the research approach, to generate a piece of statistical information; and the processing unit performs calculation for the related first parameter, second parameter, and various pieces of research data according to a statistical-test algorithm, to generate a statistical test, wherein the statistical test is relevance and a causal relationship between the first parameter and the second parameter; and a display unit, connected to the processing unit, wherein the display unit displays a piece of integration information, wherein the processing unit integrates the first parameter, the second parameter, the statistical information, and the statistical test into the integration information according to an integration algorithm.

2. The data analysis system according to claim 1, further comprising a database, connected to the transmission unit, wherein the database stores the to-be-analyzed data.

3. The data analysis system according to claim 1, wherein the statistical information is one or any combination of an occurrence rate, an occurrence density ratio, a relative risk, and an odds ratio.

4. The data analysis system according to claim 3, wherein the processing unit calculates, according to an occurrence rate algorithm, at least one occurrence rate related to the various pieces of research data, and performs analysis and calculation according to each occurrence rate, to obtain an occurrence rate ratio.

5. The data analysis system according to claim 4, wherein the research approach comprises a first research approach, a second research approach, and a third research approach; and when the control unit selects the first research approach, the processing unit performs calculation, to obtain the statistical information related to the first parameter, the second parameter, and the various pieces of research data, wherein the statistical information comprises at least one occurrence rate;

when the control unit selects the second research approach, the processing unit performs analysis and calculation for the related first parameter, second parameter, and various pieces of research data, to generate the statistical information; or when the control unit selects the third research approach, the processing unit performs calculation, to obtain the statistical information related to the first parameter, the second parameter, and the various pieces of research data, wherein the statistical information comprises each occurrence rate, wherein the statistical information is one or a combination of a relative risk and an odds ratio.

6. The data analysis system according to claim 5, wherein when the control unit selects the first research approach, the statistical information is one or any combination of each related occurrence rate, the related relative risk, and the related odds ratio; when the control unit selects the second research approach, the statistical information is the related odds ratio; or when the control unit selects the third research approach, the statistical information is one or a combination of each related occurrence rate and the related odds ratio.

7. The data analysis system according to claim 3, wherein the processing unit further performs analysis and calculation for the corresponding first parameter and second parameter according to an occurrence density algorithm, to generate at least one occurrence density; and the processing unit performs analysis and calculation according to each occurrence density, to obtain at least one occurrence density ratio.

8. The data analysis system according to claim 1, wherein the statistical-test algorithm comprises one or a combination of a statistical hypothesis testing algorithm and a single-factor/multiple-factor analysis algorithm.

9. The data analysis system according to claim 8, wherein the statistical hypothesis testing algorithm comprises one or any combination of a Chi-square test algorithm, a Fisher exact test algorithm, an independent two-sample T-test algorithm, and a Wilcoxon rank-sum test algorithm.

10. The data analysis system according to claim 8, wherein the single-factor/multiple-factor analysis algorithm comprises one or any combination of a survival analysis algorithm, a Cox proportional hazards model algorithm, a Poisson regression model algorithm, and a logistic regression model algorithm.

11. A data analysis method, comprising:
generating, by a control unit, a first parameter, a second parameter, and a research approach according to an operation instruction of a user;
obtaining, from a piece of to-be-analyzed data, at least one piece of research data corresponding to the first parameter and the second parameter, wherein the first parameter is a to-be-analyzed cause item, and the second parameter is a to-be-analyzed result item;
receiving, by a transmission unit, various pieces of research data;
analyzing, by a processing unit, the first parameter, the second parameter, and the various pieces of research data according to a statistical algorithm, to generate a piece of statistical information;
performing, by the processing unit according to a statistical-test algorithm, calculation for the related first parameter, second parameter, and various pieces of research data, to generate a statistical test, wherein the statistical test is relevance and a causal relationship between the first parameter and the second parameter;
integrating, by the processing unit, the first parameter, the second parameter, the statistical information, and the statistical test into integration information according to an integration algorithm; and
displaying, by a display unit, the integration information.

12. The data analysis method according to claim 11, wherein the statistical algorithm is an occurrence rate algorithm; the processing unit calculates, according to the occurrence rate algorithm, at least one occurrence rate related to the various pieces of research data and corresponding to the first parameter and the second parameter; and the processing unit performs analysis and calculation by using each occurrence rate, to obtain an occurrence rate ratio.

13. The data analysis method according to claim 12, wherein the research approach comprises a first research approach, a second research approach, and a third research approach; and the control unit selects the first research approach; and
the processing unit performs calculation, to obtain the statistical information related to the first parameter, the second parameter, and the various pieces of research data, wherein the statistical information comprises at least one occurrence rate;
the control unit selects the second research approach; and the processing unit performs calculation, to obtain the statistical information related to the first parameter, the second parameter, and the various pieces of research data; or the control unit selects the third research approach; and the processing unit performs calculation, to obtain the statistical information related to the first parameter, the second parameter, and the various pieces of research data, wherein the statistical information comprises each occurrence rate, wherein the statistical information is one or a combination of a relative risk and an odds ratio.

14. The data analysis method according to claim 13, wherein when the control unit selects the first research approach, the statistical information is one or any combination of each related occurrence rate, the related relative risk, and the related odds ratio; when the control unit selects the second research approach, the statistical information is the related odds ratio; or when the control unit selects the third research approach, the statistical information is one or a combination of each related occurrence rate and the related odds ratio.

15. The data analysis method according to claim 11, further comprising:

performing, by the processing unit, analysis and calculation according to an occurrence density algorithm, to obtain at least one occurrence density corresponding to the first parameter and the second parameter; and performing, by the processing unit, analysis and calculation according to each occurrence density, to obtain at least one occurrence density ratio.

16. The data analysis method according to claim 11, wherein the statistical-test algorithm comprises one or a combination of a statistical hypothesis testing algorithm and a single-factor/multiple-factor analysis algorithm.

17. The data analysis method according to claim 11, wherein the statistical hypothesis testing algorithm comprises one or any combination of a Chi-square test algorithm, a Fisher exact test algorithm, an independent two-sample T-test algorithm, and a Wilcoxon rank-sum test algorithm.

18. The data analysis method according to claim 11, wherein the single-factor/multiple-factor analysis algorithm comprises one or any combination of a survival analysis algorithm, a Cox proportional hazards model algorithm, a Poisson regression model algorithm, and a logistic regression model algorithm.

* * * * *